United States Patent
Connor et al.

(10) Patent No.: US 6,858,739 B2
(45) Date of Patent: Feb. 22, 2005

(54) INDOLE AND BENZIMIDAZOLE 15-LIPOXYGENASE INHIBITORS

(75) Inventors: David Thomas Connor, Ann Arbor, MI (US); William Howard Roark, Ann Arbor, MI (US); Roderick Joseph Sorenson, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 30 days.

(21) Appl. No.: 10/362,292

(22) PCT Filed: May 8, 2001

(86) PCT No.: PCT/US01/14798

§ 371 (c)(1),
(2), (4) Date: Feb. 21, 2003

(87) PCT Pub. No.: WO01/96299

PCT Pub. Date: Dec. 20, 2001

(65) Prior Publication Data

US 2004/0038943 A1 Feb. 26, 2004

Related U.S. Application Data

(60) Provisional application No. 60/211,489, filed on Jun. 14, 2000.

(51) Int. Cl.$^7$ ............................................. C07D 209/10
(52) U.S. Cl. ...................................................... 548/491
(58) Field of Search ........................................ 548/491

(56) References Cited

U.S. PATENT DOCUMENTS

| 5,958,950 A | 9/1999 | Padia et al. .................. 514/321 |
| 6,001,866 A | 12/1999 | Cornicelli et al. .......... 514/410 |
| 6,534,521 B2 | 3/2003 | Connor et al. |

FOREIGN PATENT DOCUMENTS

WO          WO 9806703          2/1998

OTHER PUBLICATIONS

Gastpar et al., "Methoxy–Substituted 3–Formyl–2– phenylindoles Inhibit Tubulin Polymerization", *J. Med. Chem.*, vol. 41, No. 25, 1998; pp. 4965–4972.

Johnson et al., "Palladium (0)–Catalysed Arylations using Pyrrole and Indole 2–Boronic Acids", *Synnlett*, vol. 9, 1998, pp. 1025–1027.

Fagnola et al., "Solid–Phase Synthesis of Indoles Using the Palladium–Catalysed Coupling of Alkynes with iodoaniline Derivatives", *Tetrahedrom Letters*, vol. 38, No. 13, 1997 pp. 2307–2310.

Rozhkov et al., "Synthesis of 2–Aryl– and 2–Hetaryl–4, 6–dinitroindoles from 2,4,6–Trinitrotoluene", *Synthesis*, No. 12, 1999, pp. 2065–2070.

*Chemical Abstracts*, vol. 107, No. 6, 1987, abstract No. 48792q.

R. K. Bansal, et al, "Mass Spectral Studies of some Fluorinated Indoles and Benzindoles", J. Indian Chem. Soc., vol. LXIII, Sep. 1986, pp. 850–851.

*Primary Examiner*—Taofiq Solola
(74) *Attorney, Agent, or Firm*—Eric J. Baude; Claude F. Purchase, Jr.

(57) ABSTRACT

This invention provides indole and benzimidazole 15-lipoxygenase (15-LO) inhibitors of the formula where one of $Y_1$ and $Y_2$ is CH, N, or NH, and the other is $R_3$ includes H, halo, $HN_2$, COOH, alkyl; $R_4$ includes halo, alkyl, and alkoxy; Z is C, CH, or $NR_5$; $R_5$ is H or oxycabonyl; and each X is independently H, alkyl, alkoxy, or halo.

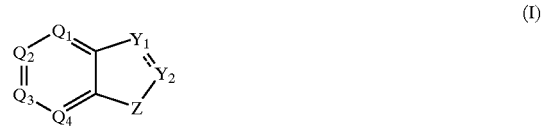

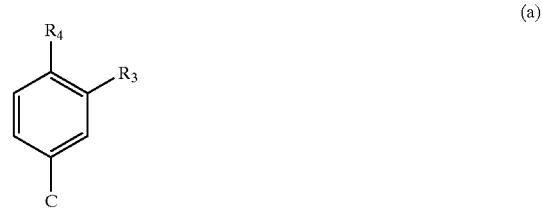

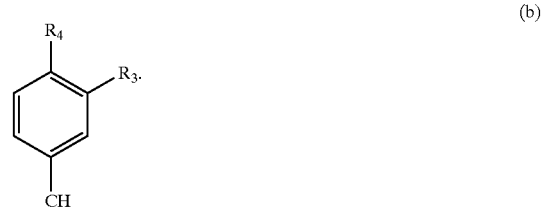

12 Claims, No Drawings

INDOLE AND BENZIMIDAZOLE 15-LIPOXYGENASE INHIBITORS

This application claims the benefit of PCT/US01/14798 filed May 8, 2001, which claims the benefit of U.S. Provisional Application Ser. No. 60/211,489 filed Jun. 14, 2000; the entire contents of each of which are hereby incorporated herein by reference.

FIELD OF THE INVENTION

This invention concerns indoles and benzimidazoles that are inhibitors of the 15-lipoxygenase enzyme, and are thus useful for treating inflammatory diseases.

BACKGROUND OF THE INVENTION

Hypercholesterolemia is a condition in mammals that can induce monocytes to migrate into the arterial wall and mature into foam cells or tissue macrophages that accumulate fatty material including cholesterol esters. The accumulation of foam cells thickens the inner lining of the artery and forms atherosclerotic plaques or lesions containing cholesterol, smooth muscle cells, and connective tissue cells. Affected arteries lose elasticity and become narrowed or obstructed by the plaques. Furthermore, atherosclerotic plaques may collect calcium, become brittle, and even rupture, triggering the formation of a blood clot or thrombus capable of occluding an artery and causing a stroke or a heart attack. In addition to the arteries of the brain and heart, atherosclerosis may affect the arteries of the arms, legs, kidneys, and other vital organs.

Lipoxygenases are enzymes that catalyze the oxidation of polyunsaturated fatty acids such as the low-density lipoproteins related to cholesterol and necessary for foam cell formation. For example, 15-lipoxygenase (15-LO) oxidizes esterified polyenoic fatty acids. 15-LO has been implicated in inflammatory disorders and in the origin and recruitment of foam cells (see, e.g., Harats, et al., *Trends Cardiovasc. Med.*, 1995;59(1):29–36). In addition to modifying lipoproteins relating to the formation of foam cells, 15-LO also mediates an inflammatory reaction in the atherosclerotic lesion. In human monocytes, 15-LO is induced by the cytokine IL-4.

Inhibitors of 15-LO are therefore useful to prevent and treat inflammatory diseases such as asthma, psoriasis, osteoarthritis, rheumatoid arthritis, colorectal cancer, and atherosclerosis. For example, Sendobry, et al., *British J. of Pharmacology*, 1977;120:1199–1206 show suppression of atherogenesis in rabbits fed a high-fat diet and treated with a 15-LO inhibitor.

Numerous indole and benzimidazole compounds are known, and many are said to be useful as antiinflammatory agents. For example, Gastpar et al. describe a series of indole anticancer agents, *J. Med Chem.*, 1998;41:4965–4972. Connor et al. describe certain 2-phenyl benzimidazoles as antiinflammatory agents (WO 98/06703). Cornicelli et al. describe both indole and benzimidazole antiinflammatory agents in U.S. Pat. No. 6,001,866.

An object of this invention is to provide new indole and benzimidazole compounds that are potent inhibitors of 15-LO.

SUMMARY OF THE INVENTION

The invention provides compounds of Formula I:

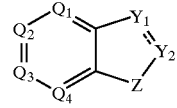

I wherein:
each of $Q_1$, $Q_2$, $Q_3$, and $Q_4$ is independently CX, where X is independently H, halo, $C_1$–$C_4$ alkyl, $C_1$–$C_4$ alkenyl, $C_1$–$C_4$ alkynyl, hydroxyl, $C_1$–$C_4$ hydroxyalkyl, amino, (amino)sulfonyl, N-acetyl, O-acetyl, $C_1$–$C_4$ thioalkyl, $C_1$–$C_4$ alkoxy, $COOR_6$, $SO_3Na$, $SO_3H$, $SO_2NH_2$, cyano, phosphonic acid, phosphonic acid esters, $C_1$–$C_6$ alkanoic acid, $C_1$–$C_6$ alkanoic acid esters, carbamic acid, carbamic acid esters, $CH_2NH_2$, acetyl, di($C_1$–$C_4$alkyl)amino, or nitro;
one of $Y_1$ and $Y_2$ is CH, N, or NH, and the other of $Y_1$ and $Y_2$ is

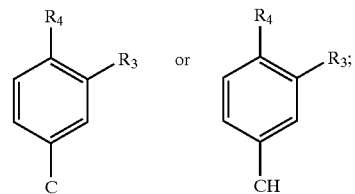

— is a bond when one of $Y_1$ and $Y_2$ is CH or N, and the other one of $Y_1$ and $Y_2$ is

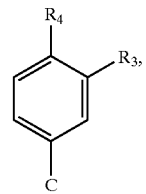

and is absent when $Y_1$ or $Y_2$ is NH;
$R_3$ is selected from H, $NHR_a$, halo, $C_1$–$C_4$ haloalkyl, COOH, —COO($C_1$–$C_6$ alkyl), (phenyl)$C_1$–$C_6$ alkoxy, hydroxy, $C_1$–$C_6$ alkoxy, —NH(CO)($C_1$–$C_6$ alkyl), nitro, and $C_1$–$C_6$ aminoalkyl, where $R_a$ is H, $C_1$–$C_4$ alkyl, $C_3$–$C_8$ cycloalkyl, phenyl, $C_2$–$C_6$ heteroaryl, benzyl, $CH_2$—($C_2$–$C_6$ heterocyclic radical), or —M—T, where M is sulfonyl, $SO_2NR_b$, $CONR_b$, or $CSNR_b$; T is $C_1$–$C_{18}$ alkyl, phenyl, or $C_3$–$C_6$ heterocyclic radical; and $R_b$ is H, $C_1$–$C_4$ alkyl, phenyl, benzyl, $C_1$–$C_6$ alkoxy, $C_1$–$C_6$ alkanoic acid alkyl ester, lower alkylamino carbamate, 1-phenethyl, 2-phenethyl, aminosulfonylphenyl, an amino acid radical selected from serine, phenylalanine, histidine, tryptophan, or tyrosine wherein hydroxy or carboxy groups may be protected or unprotected linked by the amino nitrogen or $C_2$–$C_6$ heterocyclic radical; provided where Y is N and Z is $NR_5$, $R_3$ is $SO_2T$, $SO_2NR_bT$, $CONR_bT$, or $CSNR_bT$;
$R_4$ is selected from methoxy, ethoxy, thiomethoxy, fluoro, chloro, methyl, and ethyl;
Z is $NR_5$, C, or CH, where $R_5$ is H, [phenyl($C_1$–$C_4$ alkyl)]oxycarbonyl, ($C_1$–$C_4$ alkyl)oxycabonyl, ($C_3$–$C_8$ cycloalkyl)oxycarbonyl, ($C_3$–$C_8$ cycloalkyl)-($C_1$–$C_4$ alkyl)oxycarbonyl, or ($C_6$–$C_{10}$ aryl)oxycarbonyl;

wherein each hydrocarbyl or heterocyclic radical above is optionally substituted with between 1 and 3 substituents independently selected from chloro, fluoro, $C_1$–$C_4$ alkyl, $C_3$–$C_6$ cycloalkyl, $C_1$–$C_4$ alkenyl, $C_1$–$C_4$ alkynyl, phenyl hydroxyl, $C_1$–$C_4$ hydroxyalkyl, amino, (amino)sulfonyl, N-acetyl, O-acetyl, $C_1$–$C_4$ thioalkyl, $C_1$–$C_4$ alkoxy, $COOR_6$, $SO_3Na$, $SO_3H$, $SO_2NH_2$, cyano, phosphonic acid, phosphonic acid esters, methylphosphonic acid, methylphosphonic acid esters, $C_1$–$C_6$ alkanoic acid, $C_1$–$C_6$ alkanoic acid esters, carbamic acid, carbamic acid esters, $CH_2NH_2$, acetyl, di($C_1$–$C_4$ alkyl)amino, and nitro, wherein each substituent alkyl, cycloalkyl, alkenyl, alkynyl or phenyl is in turn optionally substituted with between 1 and 3 substituents independently selected from halo, $C_1$–$C_3$ alkyl, hydroxyl, amino, and nitro; and $R_6$ is H or $C_1$–$C_6$ alkyl;

or a pharmaceutically acceptable salt or $C_1$–$C_8$ alkyl ester thereof.

Preferred compounds of Formula I and those wherein $R_3$ is NH $CONR_bT$ or NH $CSR_bT$.

Especially preferred are compounds wherein $R_b$ is hydrogen and T is phenyl or phenyl substituted with 1 or 2 groups such as halo, carboxy, hydroxy, alkoxy, amino, nitro, alkylphosphonate, and cyano.

Preferred compounds have Formula II

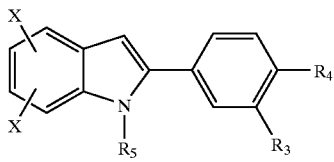

II wherein $R_3$, $R_4$, $R_5$, and X are as defined above.

Another preferred group of invention compounds have Formula III

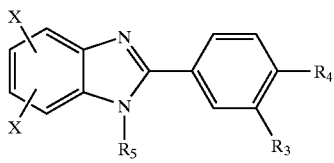

III wherein $R_3$, $R_4$, $R_5$, and X are as defined above.

Also preferred are compounds of Formula IV

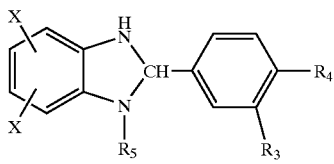

IV wherein $R_3$, $R_4$, $R_5$, and X are as defined above.

Still further preferred compounds have Formula V

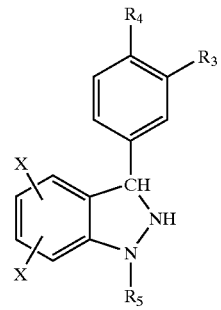

V wherein $R_3$, $R_4$, $R_5$, and X are as defined above.

The invention also provides pharmaceutical compositions comprising compounds of Formula I, together with a carrier, as well as methods of making the disclosed compounds according to traditional synthetic organic routes and combinatorial or matrix chemistry routes according to the principles set forth herein. Preferred compositions comprise a compound of Formulas II through V with a carrier.

The invention also provides methods for treating mammals with diseases relating to the 15-LO cascade. These methods are for treating, preventing, or ameliorating the related condition or disease. These methods include the following.

A method for inhibiting 15-LO, said method comprising administering to a patient in need of 15-lipoxygenase inhibition a pharmaceutically-effective amount of a compound of Formula I.

A method for treating or preventing atherosclerosis, said method comprising administering to a patient at risk or in need of such treatment a therapeutically-effective amount of a compound of Formula I.

A method for inhibiting the chemotaxis of monocytes, said method comprising administering to a patient in need of inhibition of monocytic migration a therapeutically-effective amount of a compound of Formula I.

A method for treating or preventing inflammation, said method comprising administering to patient at risk or in need of such treatment a therapeutically-effective amount of a compound of Formula I.

A method for treating or preventing stroke, said method comprising administering to a patient at risk or in need of such treatment a therapeutically-effective amount of a compound of Formula I.

A method for treating or preventing coronary artery disease, said method comprising administering to a patient at risk or in need of such treatment a therapeutically-effective amount of a compound of Formula I.

A method for treating or preventing asthma, said method comprising administering to patient at risk or in need of such treatment a therapeutically-effective amount of a compound of Formula I.

A method for ting or preventing arthritis, said method comprising administering to patient at risk or in need of such treatment a therapeutically-effective amount of a compound of Formula I.

A method for treating or preventing colorectal cancer, said method comprising administering to a patient at risk or in need of such treatment a therapeutically-effective amount of a compound of Formula I.

A method for treating or preventing psoriasis, said method comprising administering to a patient at risk or in need of such treatment a therapeutically-effective amount of a compound of Formula I.

Other aspects and features of the invention will be apparent from the disclosure, examples, and claims set forth below.

DETAILED DESCRIPTION OF THE INVENTION

The invention provides compounds of Formula I and methods of making and using them. Other features of the invention, and preferred embodiments thereof, will become apparent from the examples and claims below.

A. Terms

Certain terms used herein are defined below and by their usage throughout this disclosure.

Alkyl groups include aliphatic (i.e., hydrocarbon radicals containing hydrogen and carbon atoms) with a free valence. Alkyl groups are understood to include straight chain and branched structures. Preferred alkyl groups have from 1 to 6 carbon atoms. Examples of typical alkyl groups include methyl, ethyl, propyl, isopropyl, butyl, n-butyl, isobutyl, t-butyl, pentyl, isopentyl, 2,3-dimethylpropyl, hexyl, 2,3-dimethyl hexyl, 1,1-dimethylpentyl, heptyl, and octyl. Cycloalkyl groups are $C_3-C_8$ cyclic structures, examples of which include cyclopropyl, cyclobutyl, cyclopentyl, cyclohexyl, and cyclooctyl.

Alkyl and cycloalkyl groups can be substituted with 1, 2, 3 or more substituents which are independently selected from halo (fluoro, chloro, bromo, or iodo), hydroxy, amino, alkoxy, alkylamino, dialkylamino, cycloalkyl, aryl, aryloxy, arylalkyloxy, heterocyclic radical, (heterocyclic radical)oxy, (amino)sulfonyl, N-acetyl, O-acetyl, $C_1-C_4$ thioalkyl, $C_1-C_4$ alkoxy, $COOR_6$, $SO_3Na$, $SO_3H$, $SO_2NH_2$, cyano, $CH_2NH_2$, acetyl, trifluoromethyl, and nitro. Specific examples include COOH, thiomethyl, methoxy, ethoxy, dimethylamino, ethylmethylamino, diethylamino, and chloro. Other examples include fluoromethyl, hydroxyethyl, 2,3-dihydroxyethyl, (2- or 3-furanyl)methyl, cyclopropylmethyl, methylcyclopropyl, benzyloxyethyl, (3-pyridinyl)methyl, (2- or 3-furanyl)methyl, (2-thienyl)ethyl, hydroxypropyl, aminocyclohexyl, 2-dimethylaminobutyl, methoxymethyl, 2-ethoxycyclopentyl, N-pyridinylethyl, diethylaminoethyl, and cyclobutylmethyl.

Alkenyl groups are analogous to alkyl groups, but have at least one double-bond (two adjacent $sp^2$ carbon atoms). Depending on the placement of a double-bond and substituents, if any, the geometry of the double-bond may be entgegen (E), zusammen (Z), cis, or trans. Similarly, alkynyl groups have at least one triple-bond (two adjacent sp carbon atoms). Unsaturated alkenyl or alkynyl groups may have one or more double- or triple-bonds, respectively, or a mixture thereof; like alkyl groups, they may be straight chain or branched, and they may be substituted as described above and throughout the disclosure. Examples of alkenyls, alkynyls, and substituted forms include cis-2-butenyl, trans-2-butenyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4-hydroxy-3-butynyl, 3-(3-fluorophenyl)-2-propynyl, and 2-methyl-2-propenyl.

The foregoing groups are referred to collectively as "hydrocarbyl" groups. More general forms of substituted hydrocarbyls include hydroxyalkyl, hydroxyalkenyl, hydroxyalkynyl, hydroxycycloalkyl, hydroxyaryl, and corresponding forms for the prefixes amino-, halo- (e.g., fluoro-, chloro-, or bromo-), nitro-, alkyl-, phenyl-, cycloalkyl- and so on, or combinations of substituents. According to Formula I, therefore, substituted alkyls include hydroxyalkyl, aminoalkyl, nitroalkyl, haloalkyl, alkylalkyl (branched alkyls, such as methylpentyl), (cycloalkyl)alkyl, phenylalkyl, alkoxy, alkylaminoalkyl, dialkylaminoalkyl, arylalkyl, aryloxyalkyl, arylalkyloxyalkyl, (heterocyclic radical)alkyl, and (heterocyclic radical)oxyalkyl and so on. Where $R_a$ or $R_b$ are both phenyl, for example, $R_a$ thus includes 3-halo-4-hydroxyphenyl, 3-(fluoro or chloro)-4-nitrophenyl, 3,4-dichlorophenyl, 3,5-dichlorophenyl, 3,5-difluorophenyl, 3-hydroxy-4-nitrophenyl, 4-hydroxy-3-nitrophenyl, 3-chlorophenyl, 4-chlorophenyl, 2-fluorophenyl, 3-fluorophenyl, 4-fluorophenyl, 3,4-difluorophenyl, 2,3-difluorophenyl, 2,4-difluorophenyl, 3-trifluoromethylphenyl, 4-trifluoromethylphenyl, 3-aminophenyl, 4-aminophenyl, 3,5-dimethylphenyl, 3-methylphenyl, 4-methylphenyl, 3-nitrophenyl, 4-nitrophenyl, 3-nitro-4-chlorophenyl, 3-cyanophenyl, 4-cyanophenyl, 3-methyleneaminophenyl, 4-methyleneaminophenyl, 3-hydroxyphenyl, 4-hydroxyphenyl, 3,4-dihydroxyphenyl, 4-chloro-3-trifluoromethylphenyl, 3-carbomethoxyphenyl, 4-carbomethoxyphenyl, bis(3,5-trifluoromethyl)phenyl, 4-t-butylphenyl 4-n-butylphenyl, 4-isopropylphenyl, 3-acetylphenyl, 4-sulfonic acid (e.g., sodium salt), 3-carboxyphenyl, 4-carboxyphenyl, 3-methoxyphenyl, 4-methoxyphenyl, 3,4-dimethoxyphenyl, 4-acetamidophenyl, 3-amino-4-halophenyl, 3-alkoxy-4-halophenyl, 3-halo-4-alkylaminophenyl, 4-(N,N-dimethylamino)phenyl, 3-cycloalkylphenyl, 3(3',5'-dihalophenyl)-4-nitrophenyl, 4-aryloxyphenyl, arylalkyloxyphenyl, heterocyclic radical phenyl (heterocyclic radical)oxy, 4-sulfamoylphenyl (or 4-aminosulfonylphenyl), 3-(alkylcarbonyloxy)phenyl such as 3-acetylphenyl, and 3-($C_1-C_4$ thioalkyl)phenyl.

Similarly, the invention features analogous examples of substituted $R_a$ on a heterocyclic radical. Heterocyclic radicals, which include but are not limited to heteroaryls, include cyclic and bicyclic ring moieties having between 1 and 4 heteroatoms selected independently from O, S, and N, and having from 2 to 11 carbon atoms. The rings may be aromatic or nonaromatic, with $sp^2$ or $sp^3$ carbon atoms. Examples include: furyl, oxazolyl, isoxazolyl, thienyl, thiophenyl, thiazolyl, pyrrolyl, imidazolyl, triazolyl such as 1,3,4-triazolyl, tetrazolyl, thiazolyl, oxazolyl, xanthenyl, pyronyl, pyridyl, pyrimidyl, triazinyl, pyrazinyl, pyridazinyl, indolyl, and pyrazolyl. Further examples of heterocyclic radicals include piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, and octahydrobenzofuranyl. Particularly preferred heterocyclic radicals include 2-pyridyl, 3-pyridyl, 4-pyridyl, 3-picolinyl, 2-thienyl, 3-thienyl, 2-furyl, 3-furyl, dansyl, 8-quinoyl, 2-acetamido-4-thiazole, and imidazolyl. These may be substituted with one or more substituents such as halo, $C_1-C_4$ alkoxy, $COOR_6$, $SO_3Na$, $SO_3H$, $SO_2NH_2$, cyano, $CH_2NH_2$, acetyl, trifluoromethyl. Examples of substituted heterocyclic radicals include chloropyranyl, methylthienyl, fluoropyridyl, amino-1-,4-benzisoxazinyl, nitroisoquinolinyl, and hydroxyindolyl. Heterocyclic radicals can be bonded through a carbon atom or a heteroatom.

The term "patient" means a mammal such as a human or a domestic animal such as a dog, cat, horse, bovine, porcine, and sheep.

The term "effective amount" means that quantity of a compound of Formula I that inhibits the 15-LO enzyme in a patient to an extent that results in prevention or treatment of an inflammatory condition or otherwise benefits a patient by virtue of having endogenous 15-LO enzymes inhibited.

The term "halo" includes fluoro, chloro, bromo, and iodo.

B. Compounds

The invention provides compounds of Formula I. Preferred compounds include compounds of Formula I wherein: (a) $Q_2$ and $Q_3$ are the same; (b) $Q_2$ and $Q_3$ are each C—F; (c) $Q_2$ and $Q_3$ are each C—Cl; (d) $Q_2$ and $Q_3$ are each C—H; (e) $R_a$ is H, methyl, ethyl, hydroxy ethyl, furanyl, phenyl, substituted phenyl, benzyl, or substituted benzyl; (f) $R_a$ comprises sulfonyl, $CONR_b$, or $CSNR_b$; (g) $R_b$ is H, dichlorophenyl, carboxylic acid phenyl, aminosulfonylphenyl, dicarboxylic acid phenyl, or carboxylic acid benzyl; (h) or combinations of the above. Preferred compounds are further defined by Formulas II, III, IV, and V.

Specific examples of compounds are provided in the synthetic Examples 1 through 54 below. Especially preferred compounds provided by this invention include:

5-(1H-Indol-2-yl)-2-methoxy-phenylamine EXAMPLE 1);
5-(5,6-Difluoro-1H-indol-2-yl)-2-methoxy-phenylamine (EXAMPLE 3);
4-{3-[5-(5,6-Difluoro-1H-indol-2-yl)-2-methoxy-phenyl]-thioureido}-benzoic acid (EXAMPLE 5);
3-{3-[5-(5,6-Difluoro-1H-indol-2-yl)-2-methoxy-phenyl]-thioureido}-benzoic acid (EXAMPLE 6);
N-[5-(5,6-Difluoro-1H-indol-2-yl)-2-methoxy-phenyl]-methanesulfonamide (EXAMPLE 7);
Thiophene-2-sulfonic acid [5-(5,6-difluoro-1H-indol-2-yl)-2-methoxy-phenyl]-amide EXAMPLE 9);
3-Amino-N-[5-(5,6-difluoro-1H-indol-2-yl)-2-methoxy-phenyl]-benzenesulfonamide (EXAMPLE 16);
[5-(5,6-Difluoro-1H-indol-2-yl)-2-methoxy-phenyl]-(3-trifluoro-methylphenyl)-amine (EXAMPLE 22);
1-[5-(5,6-Difluoro-1H-indol-2-yl)-2-methoxy-phenyl]-3-(2-hydroxy-ethyl)-thiourea (EXAMPLE 37);
(2-{3-[5-(5,6-Difluoro-1H-indol-2-yl)-2-methoxy-phenyl]-thioureido}-ethyl)-carbamic acid tert-butyl ester (EXAMPLE 38);
1-[5-(5,6-Difluoro-1H-indol-2-yl)-2-methoxy-phenyl]-3-pyridin-3-yl-thiourea (EXAMPLE 41);
[5-(5,6-Difluoro-1H-indol-2-yl)-2-methoxy-phenyl]-(3-hydroxy-4-nitro-benzyl)-amine (EXAMPLE 48);
5-(5,6-Difluoro-1H-indol-2-yl)-2-methoxy-phenyl]-(4-hydroxy-3-nitro-benzyl)-amine EXAMPLE 49);
4-[5-(5,6-Difluoro-1H-indol-2-yl)-2-methoxy-phenylamino]-benzoic acid methyl ester (EXAMPLE 52); and
[5-(5,6-Difluoro-1H-indol-2-yl)-2-methoxy-phenyl]-(3-benzyloxy-phenyl)-amine (EXAMPLE 53).

Additional preferred compounds of Formula I include the following:

5-(1H-Indol-2-yl)-2-methoxy-phenylamine hydrochloride;
1-(3,5-Dichloro-phenyl)-3-[5-(1H-indol-2-yl)-2-methoxy-phenyl]-thiourea;
5-(5,6-Difluoro-1H-indol-2-yl)-2-methoxy-phenylamine hydrochloride;
1-(3,5-Dichloro-phenyl)-3-[5-(5,6-difluoro-1H-indol-2-yl)-2-methoxy-phenyl]-thiourea;
4-{3-[5-(5,6-Difluoro-1H-indol-2-yl)-2-methoxy-phenyl]-thioureido}-benzoic acid sodium salt;
3-{3-[5-(5,6-Difluoro-1H-indol-2-yl)-2-methoxy-phenyl]-thioureido}-benzoic acid;
3,5-Dichloro-N-[5-(5,6-difluoro-1H-indol-2-yl)-2-methoxy-phenyl]-benzenesulfonamide;
5-(5,6-Dichloro-1H-benzoimidazol-2-yl)-2-methoxy-phenylamine;
2-(3-Amino-4-methoxy-phenyl)-5,6-dichloro-benzoimidazole-1-carboxylic acid benzyl ester;
5,6-Dichloro-2-[4-methoxy-3-(thiophene-2-sulfonylamino)phenyl]-benzoimidazole-1-carboxylic acid benzyl ester;
3-{[5-(5,6-Difluoro-1H-indol-2-yl)-2-methoxy-phenylamino]-methyl}-phenol;
[5-(5,6-Difluoro-1H-indol-2-yl)-2-methoxy-phenyl]-thiophen-2-ylmethyl-amine;
[5-(5,6-Difluoro-1H-indol-2-yl)-2-methoxy-phenyl]-(4-methoxy-benzyl)-amine;
5,6-Dichloro-2-[3-(3-hydroxy-benzylamino)-4-methoxy-phenyl]-benzoimidazole-1-carboxylic acid benzyl ester;
4-{[5-(5,6-Difluoro-1H-indol-2-yl)-2-methoxy-phenylamino]-methyl}-benzoic acid methyl ester;
N-[5-(5,6-Difluoro-1H-indol-2-yl)-2-methoxy-phenyl]-3-nitro-benzenesulfonamide;
3-Amino-N-[5-(5,6-difluoro-1H-indol-2-yl)-2-methoxy-phenyl]-benzenesulfonamide hydrochloride;
4{3-[5-(1H-Indol-2-yl)-2-methoxy-phenyl]-thioureido}-benzenesulfonamide;
5-(5,6-Dichloro-1H-indol-2-yl)-2-methoxy-phenylamine;
3-{3-[5-(5,6-Dichloro-1H-indol-2-yl)-2-methoxy-phenyl]-thioureido}-benzoic acid;
Dodecane-1-sulfonic acid [5-(5,6-difluoro-1H-indol-2-yl)-2-methoxy-phenyl]-amide;
Dodecane-1-sulfonic acid [5-(5,6-dichloro-1H-benzoimidazol-2-yl)-2-methoxy-phenyl]-amide;
[5-(5,6-Difluoro-1H-indol-2-yl)-2-methoxy-phenyl]-(3-trifluoromethylphenyl)-amine hydrochloride;
(4-{3-[5-(1H-Indol-2-yl)-2-methoxy-phenyl]-thioureido}-benzyl)-phosphonic acid diethyl ester;
(4-{3-[5-(5,6-Difluoro-1H-indol-2-yl)-2-methoxy-phenyl]-thioureido}-benzyl)-phosphonic acid diethyl ester;
1-(3,5-Dichloro-phenyl)-3-[5-(5,6-difluoro-1H-indol-2-yl)-2-methoxy-phenyl]-urea;
[5-(1H-Indol-2-yl)-2-methoxy-phenyl]-thiourea;
1-[5-(1H-Indol-2-yl)-2-methoxy-phenyl]-3-(1-phenyl-ethyl)-thiourea;
3-Cyano-N-[5-(5,6-difluoro-1H-indol-2-yl)-2-methoxy-phenyl]-benzenesulfonamide;
[5-(1H-Indol-2-yl)-2-methoxy-phenyl]-methyl-amine;
5-{3-[5-(5,6-Difluoro-1H-indol-2-yl)-2-methoxy-phenyl]-thioureido}-isophthalic acid;
(2-{3-[5-(1H-Indol-2-yl)-2-methoxy-phenyl]-thioureido}-ethyl)-carbamic acid tert-butyl ester;
4-{3-[5-(1H-Indol-2-yl)-2-methoxy-phenyl]-thioureido}-benzoic acid;
(3-{3-[5-(1H-Indol-2-yl)-2-methoxy-phenyl]-thioureido}-phenyl)-acetic acid;
(4-{3-[5-(1H-Indol-2-yl)-2-methoxy-phenyl]-thioureido}-phenyl)-acetic acid;
1-[5-(5,6-Difluoro-1H-indol-2-yl)-2-methoxy-phenyl]-3-((S)-1-phenyl-ethyl)-thiourea;
(S)-3-tert-Butoxy-2-{3-[5-(5,6-Difluoro-1H-indol-2-yl)-2-methoxy-phenyl]-thioureido}-propionic acid tert-butyl ester;

1-[5-(5,6-Difluoro-1H-indol-2-yl)-2-methoxy-phenyl]-3-(3, 4-difluoro-phenyl)-thiourea;
1-[5-(5,6-Difluoro-1H-indol-2-yl)-2-methoxy-phenyl]-3-((1S,2S)-2-hydroxy-1-hydroxymethyl-2-phenyl-ethyl) thiourea;
1-[5-(5,6-Difluoro-1H-indol-2-yl)-2-methoxy-phenyl]-3-pyridin-3-yl-thiourea hydrochloride;
[5-(1H-indol-2-yl)-2-methoxy-phenyl]-(3-nitro-benzyl)-amine;
[5-(1H-Indol-2-yl)-2-methoxy-phenyl]-(4-nitro-benzyl)-amine;
[5-(1H-indol-2-yl)-2-methoxy-phenyl]-(3-hydroxy-4-nitro-benzyl)-amine;
[5-(1H-indol-2-yl)-2-methoxy-phenyl]-(4-hydroxy-3-nitro-benzyl)-amine;
[5-(5,6-Difluoro-1H-indol-2-yl)-2-methoxy-phenyl]-(3-nitro-benzyl)-amine;
[5-(5,6-Difluoro-1H-indol-2-yl)-2-methoxy-phenyl]-(4-nitro-benzyl)-amine;
[5-(5,6-Difluoro-1H-indol-2-yl)-2-methoxy-phenyl]-(3-hydroxy-4-nitrobenzyl)-amine hydrochloride;
5-(5,6-Difluoro-1H-indol-2-yl)-2-methoxy-phenyl]-(4-hydroxy-3-nitro-benzyl)-amine hydrochloride;
[5-(5,6-Difluoro-1H-indol-2-yl)-2-methoxy-phenyl]-(4-cyano-benzyl)-amine;
[5-(5,6-Difluoro-1H-indol-2-yl)-2-methoxy-phenyl]-(3-cyano-benzyl)-amine;
4-[5(5,6-Difluoro-1H-indol-2-yl)-2-methoxy-phenylamino]-benzoic acid methyl ester hydrochloride;
[5-(5,6-Difluoro-1H-indol-2-yl)-2-methoxy-phenyl]-(3-benzyloxy-phenyl)-amine hydrochloride; and
[5-(5,6-Dichloro-1H-indol-2-yl)-2-methoxy-phenyl]-(3-trifluoromethyl-phenyl)-amine.

C. Synthesis

The disclosed compounds can be synthesized utilizing standard organic chemistry methodologies, and typical syntheses are illustrated by to the following three Schemes, or variants thereof.

Scheme 1 illustrates the synthesis of 2-arylindoles of Formula I. The 2-arylindoles of this invention may be prepared according to methods well known in the literature, for example, as described by A. R. Katritzky and C. W. Rees, "Comprehensive Heterocyclic Chemistry, The Structure, Reactions, Synthesis, and Uses of Heterocyclic Compounds", Permagon Press, New York, 1984, Vol. 3, pp 314–369. According to Scheme 1, an appropriately substituted phenylacetyl chloride is reacted under Friedel-Crafts conditions with acceptors such as anisole in an inert solvent. Typically, the reaction is carried out at from about –40° C. to 100° C., usually from 0° C. to 25° C., in an aprotic nonpolar solvent such as dichloromethane, chloroform, dichloroethane, carbon disulfide and the like for a period of time from 1 to 72 hours, usually from 12 to 24 hours in the presence of a Lewis acid such as aluminum trichloride, boron trifluoride, titanium tetrachloride and the like, but usually in the presence of stoichiometric aluminum trichloride under anhydrous conditions. The resulting benzylphenylketone is readily dinitrated with fuming nitric acid at 0° C. to 25° C., usually at 0° C., for a period of time from about ¼ to 6 hours, usually for about 1 hour. The resulting dinitroketone is reductively cyclized using metal reducing agents such as zinc or iron in an acid solvent, typically glacial acetic acid or various strengths of hydrochloric acid. The dinitroketones may also be reduced under catalytic hydrogenation conditions under which the reductive cyclization is carried out in the presence of a metal catalyst such as Raney nickel or palladium on carbon under a positive pressure of about 1 to 50 atmospheres of hydrogen, usually about 3 atmospheres in solvents such as methanol, ethanol, acetic acid, and tetrahydrofuran for a period of time from about 3 to about 48, but usually for about 24 hours. These compounds may be further converted to thiourea or sulfonamide analogs by procedures well-known to those skilled in the art, or may be N-arylated or reductively aminated to give other analogs of the invention.

The 3-arylindoles may be prepared according to methods known in the literature (A. R Katritzky and C. W. Rees, Supra., 1984). One route is shown in Scheme 2, wherein an appropriately substituted benzoyl chloride may be reacted with an acceptor such as anisole under Friedel-Crafts conditions as described above to give a benzophenone. The benzophenone may be homologated to the diphenylacetonitrile in a variety of ways known to those skilled in the art. Thus, the benzophenone may be reduced to the corresponding benzhydrol in a variety of ways, including metal hydride or catalytic hyrogenation reductions. The resulting benzhydrol may be converted directly to the nitrile under Mitsunobu conditions or variants thereof, or may be converted to the chloride, bromide, mesylate, or tosylate and displaced by cyanide under nucleophilic substitution conditions. The benzophenone may also be directly homologated to the diphenylacetonitrile employing tosylmethylisocyanide in the presence of a strong base such as potassium-t-butoxide in a nonpolar aprotic solvent. The resulting diphenylacetonitrile may then be nitrated and reductively cyclized as described above for Scheme 1. The resulting 3-(4-methoxy-3-aminophenyl)indoles may then be elaborated to the thioureas, sulfonamides, N-aryl, and reductive amination analogs of the invention as outlined above.

The benzimidazoles of this invention may be prepared by various means known to those skilled in the art (A. R Katritzky and C. W. Rees, Supra., 1984). A preferred route to the benzimidazoles of this invention is illustrated in Scheme 3 and comprises reacting an appropriately substituted benzaldehyde with stoichiometric sodium bisulfite in a reflecting alcohol such as ethanol, from about 1 to 24 hours, preferably from 3 to 6 hours. The resulting bisulfite addition product is reacted in refluxing alcohol, preferably with an equimolar quantity of an appropriately substituted 1,2-phenylenediamine in an alcohol solvent such as ethanol for about 6 to 48 hours, preferably about 12 to 24 hours. The resulting benzimidazoles may be protected as needed with appropriately chosen amine protecting groups by methods known to those skilled in the art. The unprotected 2-(3-nitrophenyl)benzimidazoles may be reduced to the 2-(3-aminophenyl)benzimidazoles under reducing conditions described above. The protected benzimidazoles may be elaborated to thioureas, sulfonamides, N-aryl analogs, or reductive amination analogs as described above, and may then be deprotected by methods known to those skilled in the art to unmask the NH of the benzimidazole.

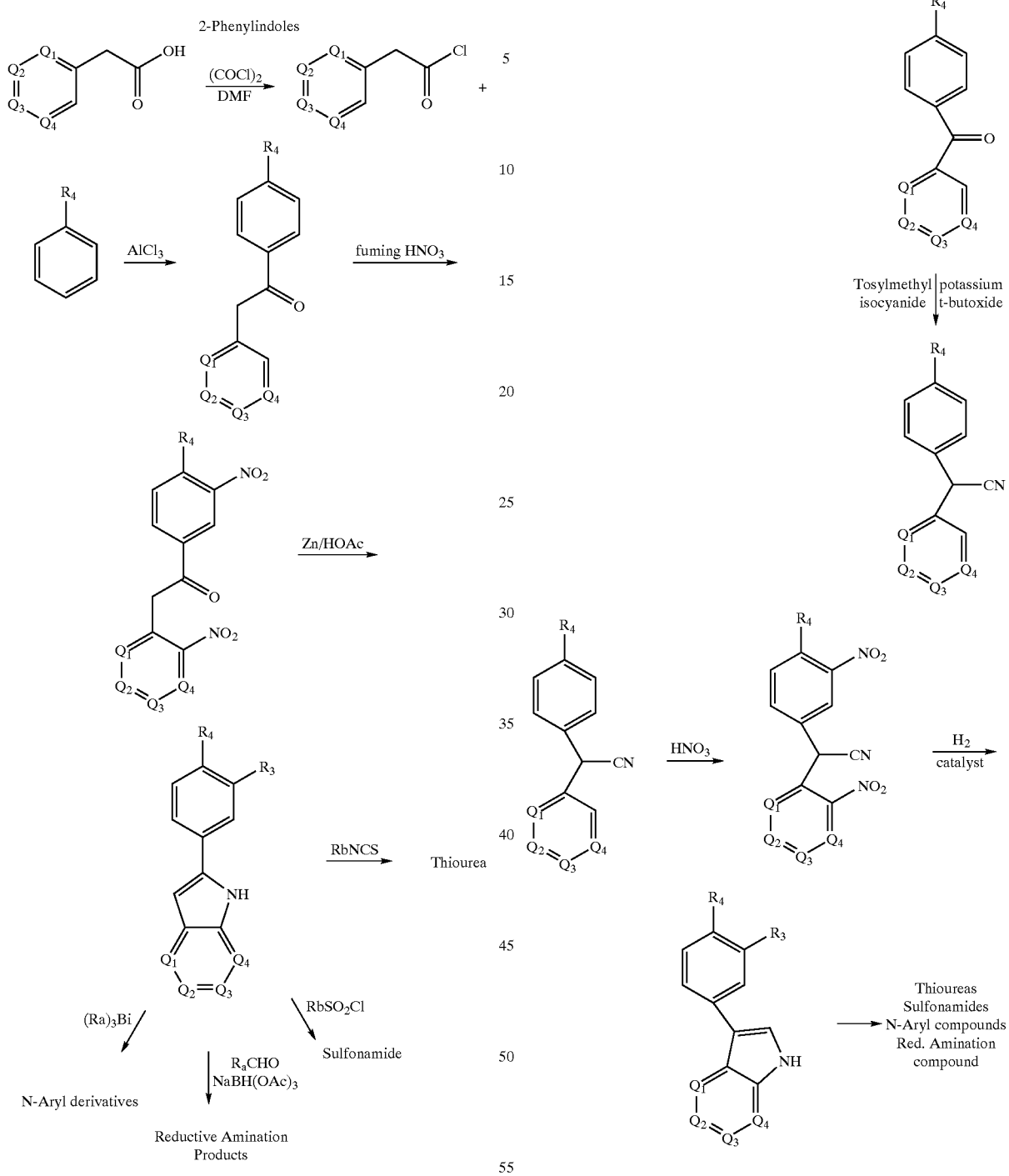
Scheme 1
2-Phenylindoles
Scheme 2
3-Phenylindoles
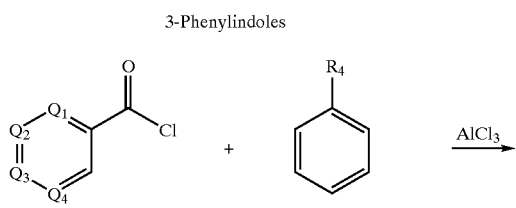
Scheme 3
2-Phenylbenzimidazoles
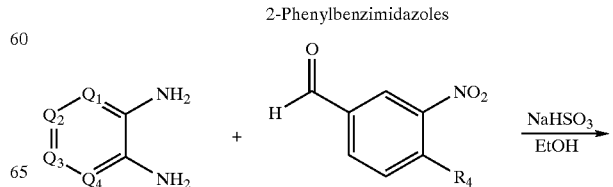

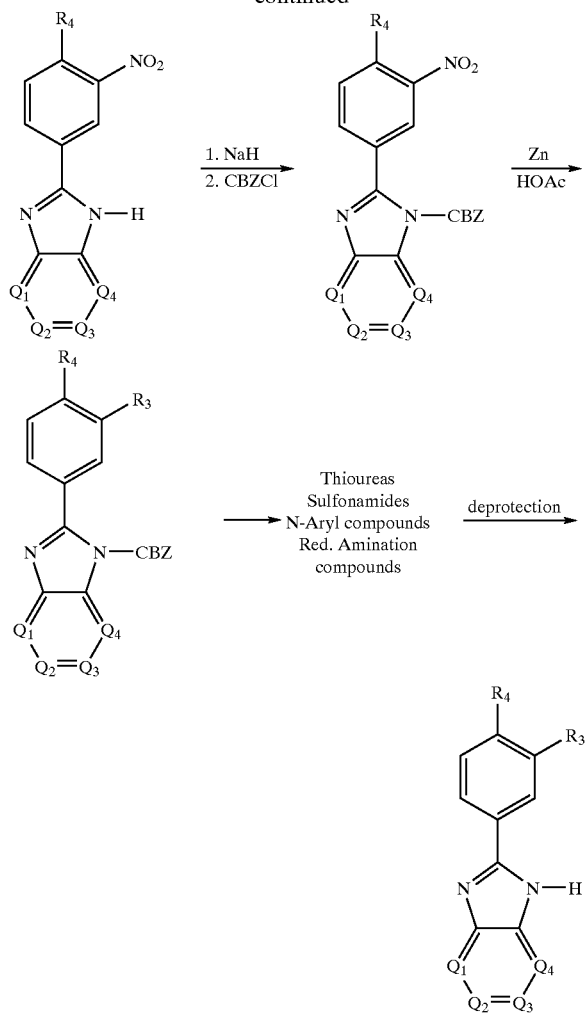

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms (at least 90%, and preferably 95%, 98%, or greater purity).

Pharmaceutically acceptable salts, esters, and amides include carboxylate salts (e.g., $C_1$–$C_8$ alkyl, cycloalkyl, aryl, heteroaryl, or heterocyclic), amino acid addition salts, esters, and amides which are within a reasonable benefit/risk ratio, pharmacologically effective, and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See, for example, S. M. Berge et al., "Pharmaceutical Salts," *J. Pharm. Sci*, 1977, 66:1–19 which is incorporated herein by reference. Representative pharmaceutically acceptable amides of the invention include those derived from ammonia, primary $C_1$–$C_6$ alkyl amines and secondary di($C_1$–$C_6$ alkyl)amines. Secondary amines include 5- or 6-membered heterocyclic or heteroaromatic ring moieties containing at least one nitrogen atom and optionally between 1 and 2 additional heteroatoms. Preferred amides are derived from ammonia, $C_1$–$C_3$ alkyl primary amines, and di($C_1$–$C_2$ alkyl)amines. Representative pharmaceutically acceptable esters of the invention include $C_1$–$C_6$ alkyl, $C_5$–$C_7$ cycloalkyl, $C_6$–$C_8$ aryl and $C_6$–$C_8$ aryl ($C_1$–$C_6$)alkyl esters. Preferred esters include methyl esters.

The invention also includes disclosed compounds having one or more functional groups (e.g., hydroxyl, amino, or carboxyl) which may be masked by a protecting group so as to avoid unwanted side reactions. Some of these masked or protected compounds are pharmaceutically acceptable; others will be useful as intermediates. Hydroxy, Amino, and Carboxyl protecting groups are well-known to those skilled in the art of synthetic organic chemistry. The use of protecting groups is fully described by Greene and Wuts, "Protecting Groups in Organic Synthesis" (John Wiley & Sons Press, 2nd ed.).

Hydroxyl Protecting Groups

Hydroxyl protecting groups include: ethers, esters, and protection for 1,2- and 1,3-diols. The ether protecting groups include: methyl, substituted methyl ethers, substituted ethyl ethers, substituted benzyl ethers, silyl ethers, and conversion of silyl ethers to other functional groups.

Substituted Methyl Ethers

Substituted methyl ethers include: methoxymethyl, methylthiomethyl, t-butylthiomethyl, (phenyldimethylsilyl)methoxymethyl, benzyloxymethyl, p-ethoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloro-ethoxy)methyl, 2-(trimethylsilyl)ethoxymethyl, tetrahydropyranyl, 3-bromotetrahydro-pyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl, and 2,3,3a,4,5,6,7,7a-octahydro-7,8,8-trimethyl-4,7-ethanobenzofuran-2-yl.

Substituted Ethyl Ethers

Substituted ethyl ethers include: 1-ethoxyethyl, 1-(2,chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilyethyl, 2-(phenylselenyl)ethyl, t-butyl, allyl, p-chlorophenyl, p-methoxyphenyl, 2,4-dinitrophenyl, and benzyl.

Substituted Benzyl Ethers

Substituted benzyl ethers include: p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyl diphenylmethyl, p-methoxyphenyldiphenylmethyl, di(p-methoxyphenyl)phenylmethyl, tri-(p-methoxyphenyl)methyl, 4-(4'-bromophenacyloxy)phenyldiphenylmethyl, 4,4',4"-tris(4,5-dichlorophthalimi dophenyl)methyl 4,4',4"-tris(levulinoyloxyphenyl)methyl, 4,4',4"tris(benzoyloxyphenyl)methyl, 3-(imidazol-1-ylmethyl)bis(4', 4"-dimethoxyphenyl)-methyl, 1,1-bis(4-methoxyphenyl)-1'-pyrenylmethyl, 9-anthryl, 9-(9-phenyl)xanthenyl 9-(9-phenyl-10-oxo)anthryl, 1,3-benzodithiolan-2-yl, and benzisothiazolyl S,S-dioxido.

Silyl Ethers

Silyl ethers include: trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxy-phenylsilyl.

Esters

Esters protecting groups include: esters, carbonates, assisted cleavage, miscellaneous esters, and sulfonates.

Esters

Examples of protective esters include: formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, and 2,4,6-trimethylbenzoate(mesitoate).

Carbonates

Carbonates include: methyl, 9-fluorenylmethyl, ethyl, 2,2, 2-trichloroethyl, 2-(trimethylsilyl)ethyl, 2-(phenylsulfonyl) ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage protecting groups include: 2-iodobenzoate, 4-azido-butyrate, 4-nitro-4-methylpentanoate, o-(dibromomethyl)benzoate, 2-formylbenzene-sulfonate, 2-(methylthiomethoxy)ethyl carbonate, 4-(methylthiomethoxymethyl)benzoate, and 2-(methylthiomethoxymethyl)benzoate.

Miscellaneous Esters

In addition to the above classes, miscellaneous esters include: 2,6-dichloro-4-methylphenoxyacetate, 2,6-dichloro-4-(1,1,3,3-tetramethylbutyl)phenoxyacetate, 2,4bis(1,1-dimethylpropyl)phenoxyacetate, chlorodiphenylacetate, isobutyrate, monosuccinoate, (E)-2-methyl-2-butenoate(tigloate), o-(methoxycarbonyl) benzoate, p-P-benzoate, α-naphthoate, nitrate, alkyl N,N, N'N'-tetramethylphosphorodiamidate, N-phenylcarbamate, borate, dimethylphosphinothioyl, and 2,4-dinitrophenylsulfenate.

Sulfonates

Protective sulfates includes: sulfate, methanesulfonate (mesylate), benzylsulfonate, and tosylate.

Protection for 1,2- and 1,3-Diols

The protection for 1,2- and 1,3-diols group includes: cyclic acetals and ketals, cyclic ortho esters, and silyl derivatives.

Cyclic Acetals and Ketals

Cyclic acetals and ketals include: methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Cyclic ortho esters include: methoxymethylene, ethoxymethylene, dimethoxy-methylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Protection for the Carbxyl Group

Esters

Ester protecting groups include: esters, substituted methyl esters, 2-substituted ethyl esters, substituted benzyl esters, silyl esters, activated esters, miscellaneous derivatives, and stannyl esters.

Substituted Methyl Esters

Substituted methyl esters include: 9-fluorenylmethyl, methoxymethyl, methylthiomethyl, tetrahydropyranyl, tetrahydrofuranyl, methoxyethoxymethyl, 2-(trimethylsilyl) ethoxy-methyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

2-Substituted ethyl esters include: 2,2,2-trichloroethyl, 2-bromoethyl, 2-chloroethyl, 2-(trimethylsily)ethyl, 2-methylthioethyl, 1,3-dithianyl-2-methyl, 2(p-nitrophenylsulfenyl)-ethyl, 2-(p-toluenesulfonyl)ethyl 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsily)-2-buten-1-yl, cinnamyl, α-methylcinnamyl, phenyl, p-(methylmercapto)-phenyl and benzyl.

Substituted Benzyl Esters

Substituted benzyl esters include: triphenylmethyl, diphenylmethyl, bis(o-nitrophenyl)methyl, 9-anthrylmethyl, 2-(9,10-dioxo)anthrylmethyl, 5-dibenzo-suberyl, 1-pyrenylmethyl,2-(trifluoromethyl)-6-chromylmethyl, 2,4, 6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, and 4-P-benzyl.

Silyl Esters

Silyl esters include: trimethylsilyl, triethylsilyl, t-butyldimethylsilyl, i-propyldimethylsilyl, phenyldimethylsilyl, and di-t-butyldimethylsilyl.

Miscellaneous Derivatives

Miscellaneous derivatives includes: oxazoles, 2-alkyl-1, 3-oxazolines, 4-alkyl-5-oxo-1,3-oxazolidines, 5-alkyl-4-oxo-1,3-dioxolanes, ortho esters, phenyl group, and pentaaminocobalt(III) complex.

Stannyl Esters

Examples of stannyl esters include: triethylstannyl and tri-n-butylstannyl.

Amides and Hydrazides

Amides include: N,N-dimethyl, pyrrolidinyl, piperidinyl, 5,6-dihydrophenanthridinyl, o-nitroanilides, N-7-nitroindolyl, N-8-nitro-1,2,3,4-tetrahydroquinolyl, and p-P-benzenesulfonamides. Hydrazides include: N-phenyl, N,N'-diisopropyl and other dialkyl hydrazides.

Protection for the Amino Group

Carbamates

Carbamates include: carbamates, substituted ethyl, assisted cleavage, photolytic cleavage, urea-type derivatives, and miscellaneous carbamates.

Carbamates

Carbamates include: methyl and ethyl, 9-fluorenylmethyl, 9-(2-sulfo)fluorenylmethyl, 9-(2,7-dibromo) fluorenylmethyl, 2,7-di-t-butyl-[9-(10,10-dioxo-10,10,10, 10-tetrahydro-thioxanthyl)]methyl, and 4-metho- xyphenacyl.

Substituted Ethyl

Substituted ethyl protective groups include: 2,2,2-trichloroethyl, 2-trimethylsilylethyl, 2-phenylethyl, 1-(1-adamantyl)-1-methylethyl, 1,1-dimethyl-2-haloethyl, 1,1dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-icyclohexylcarboxamido)-ethyl, t-butyl, 1-adamantyl, vinyl, allyl, 1-isopropylallyl, connamyl, 4-nitrocinnamyl, quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, and diphenylmethyl.

Assisted Cleavage

Protection via assisted cleavage includes: 2-methylthioethyl, 2-methylsulfonylethyl, 2-(p-toluenesulfonyl)ethyl, [2-(1,3-dithianyl)]methyl, 4-methylthiophenyl, 2,4-dimethyl-thiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolyl-methyl, and 2-(trifluoromethyl)-6-chromonylmethyl.

Photolytic Cleavage

Photolytic cleavage methods use groups such as: m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include: phenothiazinyl-(10)-carbonyl derivative, N'-p-toluenesulfonylaminocarbonyl, and N'-phenyla minothiocarbonyl.

Miscellaneous Carbamates

In addition to the above, miscellaneous carbamates include: t-amyl, S-benzyl thiocarbamate, p-cyanobenzyl, cyclobutyl, cyclohexyl, cyclopentyl, cyclopropylmethyl, p-decyloxy-benzyl, diisopropylmethyl, 2,2-dimethoxycarbonylvinyl, o-(N,N-dimethyl-carboxamido)-benzyl 1,1-dimethyl-3(N,N-dimethylcarboxamido)propyl, 1,1-dimethyl-propynyl, di(2-pyridyl)methyl, 2-furanylmethyl, 2-iodoethyl, isobornyl, isobutyl, isonicotinyl, p(p'-methoxyphenylazo)benzyl, 1-methylcyclobutyl, 1-methylcyclohexyl, 1-methyl-1-cyclopropylmethyl, 1-methyl-(3,5-dimethoxyphenyl)ethyl, 1-methyl-1-(p-henylazophenyl)-ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Amides
Amides

Amides includes: N-formyl, N-acetyl, N-chloroacetyl, N-trichloroacetyl N-trifluoroacetyl, N-phenylacetyl, N-3-phenylpropionyl, N-picolinoyl, N-3-pyridyl-carboxamide, N-benzoylphenylalanyl derivative, N-benzoyl, and N-p-phenylbenzoyl.

Assisted Cleavage

Assisted cleavage groups include: N-o-nitrophenylacetyl, N-o-nitrophenoxyacetyl, N-acetoacetyl, (N'-dithiobenzyloxycarbonylamino)acetyl N-3-(p-hydroxphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)-benzoyl, and 4,5-diphenyl-3-oxazolin-2-one.

Cyclic Imide Derivatives

Cyclic imide derivatives include: N-phthalimide, N-dithiasuccinoyl, N-2,3-diphenyl-maleoyl, N-2,5-dimethylpyrrolyl, N-1,1,4,4-tetramethyldisilylaza cyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special —NH Protective Groups

Protective groups for —NH include: N-alkyl and N-aryl amines, imine derivatives, enamine derivatives, and N-heteroatom derivatives (such as N-metal, N—N, N—P, N—Si, and N—S), N-sulfenyl, and N-sulfonyl.

N-Alkyl and N-Aryl Amines

N-alkyl and N-aryl amines include: N-methyl, N-allyl, N-[2-(triethylsilyl)ethoxyl]-methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

Imine derivatives include: N-1,1-dimethylthiomethylene, N-benzylidene, N-p-methoxybenzylidene, N-di phenylmethylene, N-[(2-pyridyl)mesityl]methylene, N-(N', N'-dimethylaminomethylene), N,N'-isopropylidene, N-p-nitrobenzylidene, N-salicylidene, N-5-chlorosalicylidene, N-(5-chloro-2-hydroxyphenyl)-phenylmethylene, and N-cyclohexylidene.

Enamine Derivative

An example of an enamine derivative is N-(5,5-dimethyl-3-oxo-1-cyclohexenyl).

N-Heteroatom Derivative

N-metal derivatives include: N-borane derivatives, N-diphenylborinic acid derivative, N-[phenyl(pentacarbonylchromium- or -tungsten)]carbenyl, and N-copper or N-zinc chelate. Examples of N—N derivatives include: N-nitro, N-nitroso, and N-oxide. Examples of N—P derivatives include: N-diphenylphosphinyl, N-dimethylthiophosphinyl, N-diphenylthiophosphinyl, N-dialkyl phosphoryl, N-dibenzyl phosphoryl, and N-diphenyl phosphoryl. Examples of N-sulfenyl derivatives include: N-benzenesulfenyl, N-o-nitrobenzenesulfenyl, N-2,4-dinitrobenzenesulfenyl, N-pentachlorobenzenesulfenyl, N-2-nitro-4-methoxy-benzenesulfenyl, N-triphenylmethylsulfenyl, and N-3-nitropyridinesulfenyl. N-sulfonyl derivatives include: N-p-toluenesulfonyl, N-benzenesulfonyl, N-2,3,6-trimethyl-4-methoxybenzenesulfonyl, N-2,4,6-trimethoxy benzenesulfonyl, N-2,6-dimethyl-4-methoxy-benzenesulfonyl, N-pentamethylbenzenesulfonyl, N-2,3,5,6-tetramethyl-4-methoxybenzene-sulfonyl, N-4-methoxybenzenesulfonyl; N-2,4,6-trimethylben zenesulfonyl, N-2,6-dimethoxy-4-methylbenzenesulfonyl, N-2,2,5,7,8-pentamethylchroman-6-sulfonyl, N-methanesulfonyl, N-β-trimethylsily lethanesulfonyl, N-9-anthracenesulfonyl, N-4-(4',8'-dimethoxynaphthyl-methyl)-benzenesulfonyl, N-benzylsulfonyl, N-trifluo romethylsulfonyl, and N-phenacyl-sulfonyl.

Disclosed compounds which are masked or protected may be prodrugs, compounds metabolized or otherwise transformed in vivo to yield a disclosed compound, e.g., transiently during metabolism. This transformation may be a hydrolysis or oxidation which results from contact with a bodily fluid such as blood, or the action of acids, or liver, gastrointestinal, or other enzymes.

The invention is further described in the working examples below. The examples are provided as illustration only, and are not to be construed as limiting the invention in any respect.

EXAMPLE 1

5-(1H-Indol-2-yl)-2-methoxy-phenylamine

Step A: 3-Nitro-4-methoxyphenyl-2'-nitrobenzyl ketone and 3-nitro-4-methoxyphenyl-4'-nitrobenzyl Ketone 4-Methoxyphenylbenzyl ketone (2.0 g, 8.8 mmol) was added in portions over 10 minutes to fuming nitric acid (10 mL) at 0° C. After completing the addition, the reaction mixture was stirred 10 minutes and was then poured into water (150 mL). The water was extracted with ethyl acetate (200 mL) and the ethyl acetate washed with saturated aqueous sodium bicarbonate solution and brine. The organic layer was dried (magnesium sulfate), filtered and concentrated to a yellow oil. The oil was filtered through silica gel (70–230 mesh) using hexanes/ethyl acetate, 7/3, v/v as eluant. The product was obtained as a solid (0.466 g) and an oil (1.95 g) both of which were mixtures. This mixture was used directly in the next step.

Step B: 5-(1H-Indol-2-yl)-2-methoxy-phenylamine

A mixture of 3-nitro-4-methoxyphenyl-2'-nitrobenzyl ketone and 3-nitro-4-methoxyphenyl-4'-nitrobenzyl ketone (1.95 g, 6.2 mmol) was taken up in glacial acetic acid (100 mL) and zinc dust (10.2 g, 325 mesh) was added in portions over 10 minutes. The reaction was very exothermic, and the reaction mixture turned red/brown. The reaction mixture was stirred 1.5 hours, then filtered, and concentrated to a dark oil. The oil was taken up in ethyl acetate, washed with saturated aqueous sodium bicarbonate solution and brine, dried (magnesium sulfate), filtered, and concentrated to a brown oil. The oil was filtered through silica gel (70–230 mesh) using hexanes/ethyl acetate, 1/1, v/v as eluant. The product was obtained as a solid (0.223 g); mp 208–209° C.

Calculated for $C_{15}H_{14}N_2O$: C, 75.61; H, 5.92; N, 11.76. Found: C, 75.34; H, 6.05; N, 11.53.

EXAMPLE 2

1-(3,5-Dichloro-phenyl)-3-[5-(1H-indol-2-yl)-2-methoxy-phenyl]-thiourea

The product from Example 1, Step B, 5-(1H-indol-2-yl)-2-methoxy-phenylamine (0.1765 g, 0.74 mmol) was mixed with 3,5-dichlorophenyl isothiocyanate (0.151 g, 0.74 mmol) in ethyl acetate (20 mL) and was heated briefly at 50° C. and then allowed to stand overnight at room temperature. The reaction mixture was concentrated to dryness, triturated with hexanes, and the insoluble material collected by filtration (0.169 g), mp 199–201° C.

Calculated for $C_{22}H_{17}Cl_2N_3OS$: C, 59.73; H, 3.87; N, 9.50. Found: C, 59.64; H, 4.07; N, 9.25.

EXAMPLE 3

5-(5,6-Difluoro-1H-indol-2-yl)-2-methoxy-phenylamine

Step A: 3,4-Difluorophenylacetyl chloride

To a solution of 3,4-difluorophenylacetic acid (10.24 g, 60.4 mmol) in tetrahydrofuran (200 mL) and dimethylformamide (5 drops) at room temperature was added in 1 mL portions oxalyl chloride (11 mL, 126 mmol). The reaction mixture was stirred 2 hours at room temperature and concentrated to an orange liquid that was used directly in the next step.

Step B: 4-Methoxyphenyl-3',4'-difluorobenzyl ketone

Aluminum trichloride (9.31 g, 70 mmol) was added in portions over 5 minutes to a mixture of anisole (12.6 g, 117 mmol) and the product from Step A, 3,4-difluorophenylacetyl chloride (60.4 mmol), in dichloromethane (500 mL) at 0° C. under nitrogen. The reaction mixture was stirred 3 days at room temperature and was then poured onto ice (300 g) and concentrated hydrochloric acid (25 mL) was added. The mixture was allowed to stand 3 hours at room temperature. The layers were separated, the organic layer washed with saturated aqueous sodium bicarbonate solution. The aqueous layer was back-extracted with dichloromethane (100 mL), the organic layers were combined, dried (magnesium sulfate), filtered, and concentrated to an orange solid. The solid was taken up in ethyl acetate, filtered, and concentrated to an oil that solidified. The solid was triturated with hexanes and collected by filtration (12.76 g), mp 82–84° C.

Step C: 2-(4,5-Difluoro-2-nitro-phenyl)-1-(4-(methoxy-3-nitro-phenyl)-ethanone

The product from Step B, 4-methoxyphenyl-3',4'-difluorobenzyl ketone (12.60 g, 48 mmol) was added over 10 minutes to fuming nitric acid (50 mL) at 0° C. The reaction mixture was stirred 1 hour at 0° C., and was then poured into a separatory funnel containing ethyl acetate (250 mL) and water (200 mL). The layers were separated, the organic layer was washed with water (200 mL), saturated aqueous sodium bicarbonate solution (100 mL), and brine (100 mL), dried (magnesium sulfate), filtered, and concentrated to a light yellow solid. The aqueous washes were back-extracted with ethyl acetate (250 mL), the organic solution washed with brine, dried (magnesium sulfate), filtered, and combined with the previous solid. This mixture was concentrated to a yellow/orange solid that was triturated with hexanes/ethyl acetate, 4/1, v/v and the insoluble portion was collected by filtration (12.78 g), mp 165–168° C.

Calculated for $C_{15}H_{10}F_2N_2O_6$: C, 51.15; H, 2.86; N, 7.95. Found: C, 51.06; H, 2.86; N, 7.83.

Step D: 5-(5,6-Difluoro-1H-indol-2-yl)-2-methoxy-phenylamine

To a mixture of the product from Step C, 2-(4,5-difluoro-2-nitro-phenyl)-1-(4-methoxy-3-nitro-phenyl)-ethanone (4.00 g, 11.3 mmol) in glacial acetic acid (100 mL) was added in portions zinc dust (28 g, 325 mesh) at 0° C. Upon adding a few portions of zinc, the reaction mixture became a solid mass. The cooling bath was removed, and the remaining zinc was added in portions; the cooling bath was replaced, and stirring was continued for 1 hour at 0° C. and 1 hour at room temperature. The zinc metal was removed by filtration and the metal was washed with ethyl acetate. The organic solution was concentrated to dryness and the residue was partitioned between ethyl acetate (200 mL) and saturated aqueous sodium bicarbonate solution (200 mL). The layers were separated, the organic layer washed with brine, dried (magnesium sulfate), filtered, and concentrated to a tan solid. The solid was triturated with hexanes/ethyl acetate, 15/1, v/v and the insoluble portion collected by filtration (2.35 g), mp 210–211° C.

Calculated for $C_{15}H_{12}F_2N_2O$: C, 65.69; H, 4.41; N, 10.21. Found: C, 65.37; H, 4.38; N, 9.99.

EXAMPLE 4

1-(3,5-Dichloro-phenyl)-3-[5-(5,6-difluoro-1H-indol-2-yl)-2-methoxy-phenyl]-thiourea The product from Example 3, 5-(5,6-difluoro-1H-indol-2-yl)-2-methoxy-phenylamine, (0.137 g, 0.5 mmol) was mixed with 3,5-dichlorophenyl isothiocyanate (0.111 g, 0.54 mmol) in ethyl acetate (10 mL) and heated briefly to 50° C. and then allowed to stand overnight at room temperature. The reaction mixture was concentrated to dryness and triturated with hexanes/ethyl acetate, and the insoluble solid collected by filtration (0.214 g), mp 203–205° C.

Calculated for $C_{22}H_{15}Cl_2F_2N_3OS$: C, 55.24; H, 3.16; N, 8.78. Found: C, 55.21; H, 3.13; N, 8.63.

EXAMPLE 5

4-{3-[5-(5,6-Difluoro-1H-indol-2-yl)-2-methoxy-phenyl]-thioureido}-benzoic acid

The product from Example 3, 5-(5,6-difluoro-1H-indol-2-yl)-2-methoxy-phenylamine, (0.274 g, 1.0 mmol) was mixed with 4-carboxyphenyl isothiocyanate (0.183 g, 1.0 mmol) in tetrahydrofuran (10 mL) and was heated briefly to 50° C. and then allowed to stand overnight at room temperature. The tetrahydrofuran was boiled off on the rotary evaporator (no vacuum) to give a solid. Ethyl acetate (5 mL) was added, and the mixture was allowed to stand overnight at room temperature. The insoluble material was collected by filtration and was a mixture. All material from the reaction mixture was taken up in tetrahydrofuran/ethyl acetate and more 4-carboxyphenyl isothiocyanate (0.020 g, 0.11 mmol) was added and the solvent was boiled off on the rotary evaporator. Ethyl acetate was added to the solid and the mixture allowed to stand overnight at room temperature. The insoluble material was collected by filtration (0.191 g), mp 201–203° C.

Calculated for $C_{23}H_{17}F_2N_3O_3S$: C, 60.92; H, 3.78; N, 9.27. Found: C, 60.58; H, 3.80; N, 9.11.

EXAMPLE 6

3-{3-[5-(5,6-Difluoro-1H-indol-2-yl)-2-methoxy-phenyl]-thioureido}-benzoic acid

The product from Example 3, 5-(5,6-difluoro-1H-indol-2-yl)-2-methoxy-phenylamine, (0.274 g, 1.0 mmol) was mixed with 3-carboxyphenyl isothiocyanate (0.185 g, 1.0 mmol) in tetrahydrofuran (10 mL) and was heated briefly to 50° C. and then allowed to stand overnight at room temperature. The tetrahydrofuran was boiled off on the rotary evaporator (no vacuum) to give a solid. Ethyl acetate (10 mL) was added, and the mixture was allowed to stand overnight at room temperature. The insoluble material was collected by filtration, washed with ethyl acetate, and air-dried to give the product (0.379 g), mp 221–223° C.

Calculated for $C_{23}H_{17}F_2N_3O_3S \cdot 0.25H_2O$: C, 60.32; H, 3.85; N, 9.18. Found: C, 60.34; H, 3.82; N, 8.99.

EXAMPLE 7

N-[5-(5,6-Difluoro-1H-indol-2-yl)-2-methoxy-phenyl]-methanesulfonamide

The product from Example 3, 5-(5,6-difluoro-1H-indol-2-yl)-2-methoxy-phenylamine, (0.276 g, 1.0 mmol) was mixed with methanesulfonic anhydride (0.300 g, 1.7 mmol), pyridine (10 mL) was added, and the reaction mixture was heated on the rotary evaporator (no vacuum) at 60° C. for 0.5 hours. The reaction mixture was allowed to stand overnight at room temperature and was then warmed to 50° C. and poured into water (100 mL), added 1N HCl (50 mL) and extracted with ethyl acetate (200 mL), washed the organic layer with water (100 mL) and brine (50 mL), dried (magnesium sulfate), filtered, and concentrated to a dark oil. The oil was filtered through silica gel (70–230 mesh) using hexanes/ethyl acetate, 3/2, v/v as eluant. The product was obtained as an orange tinted solid (0.089 g), mp 254–256° C.

Calculated for $C_{16}H_{14}F_2N_2O_3S$: C, 54.54; H, 4.00; N, 7.95. Found: C, 55.08; H, 4.22; N, 7.64.

EXAMPLE 8

3,5-Dichloro-N-[5-(5,6-difluoro-1H-indol-2-yl)-2-methoxy-phenyl]-benzenesulfonamide The product from Example 3, 5-(5,6-difluoro-1H-indol-2-yl)-2-methoxy-phenylamine, (0.274 g, 1.0 mmol) was mixed with 3,5-dichlorobenzenesulfonyl chloride (0.256 g, 1.0 mmol) and pyridine (3 mL) was added, and the reaction mixture was heated briefly to 50° C. and then allowed to stand overnight at room temperature. Water (7 mL) was added and the mixture allowed to stand 2 hours at room temperature. The mixture was partitioned between water (200 mL) and ethyl acetate (200 mL), and the organic layer was washed with 1N HCl (100 mL), water (100 mL), and brine (100 mL), dried (magnesium sulfate), filtered, and concentrated to a purple-tinted solid. The solid was triturated with hexanes/ethyl acetate, 1/1, v/v to give the product (0.355 g), mp 217–219° C.

Calculated for $C_{21}H_{14}Cl_2F_2N_2O_3S$: C, 52.19; H, 2.92; N, 5.80. Found: C, 52.23; H, 2.91; N, 5.72.

EXAMPLE 9

Thiophene-2-sulfonic acid [5-(5,6-difluoro-1H-indol-2-yl)-2-methoxy-phenyl]-amide The product from Example 3, 5-(5,6-difluoro-1H-indol-2-yl)-2-methoxy-phenylamine, (0.274 g, 1.0 mmol) was mixed with thiophene-2-sulfonyl chloride (0.192 g, 1.0 mmol) and pyridine (3 mL) was added, and the reaction mixture was heated briefly to 50° C. and then allowed to stand overnight at room temperature. Water (7 mL) was added and the mixture allowed to stand 1.75 hours at room temperature. The mixture was partitioned between water (200 mL) and ethyl acetate (200 mL) and the organic layer was washed with 1N HCl (100 mL), water (100 mL), and brine (100 mL), dried (magnesium sulfate), filtered, and concentrated to a purple-tinted solid. The solid was triturated with hexanes/ethyl acetate, 1/1, v/v to give the product (0.322 g), mp 211–213° C.

Calculated for $C_{19}H_{14}F_2N_2O_3S_2$: C, 54.28; H, 3.36; N, 6.66. Found: C, 54.29; H, 3.40; N, 6.43.

EXAMPLE 10

5,6-Dichloro-2-[4-methoxy-3-(thiophene-2-sulfonylamino)-phenyl]-benzoimidazole-1-carboxylic acid benzyl ester Step A: 5,6-Dichloro-2-(4-methoxy-3-nitro-phenyl)-1H-benzoimidazole 4-Methoxy-3-nitrobenzaldehyde (4.65 g, 27.6 mmol) and sodium bisulfite (5.79 g, 55.2 mmol) were added to ethanol (200 mL) and refluxed for 4 hours at which time 1,2-dichloro-4,5-phenylenediamine (4.56 g, 27.6 mmol) was added and the mixture was refluxed overnight. The reaction mixture was filtered while hot, and the pea-green solid washed with ethanol.(3.09 g) mp 250° C.

Calculated for $C_{14}H_9Cl_2N_3O_3$: C, 49.73; H, 2.68; N, 12.43 Found: C, 49.61; H, 2.81; N, 12.26

Step B: 5,6-Dichloro-2-(4-methoxy-3-nitro-phenyl)-benzoimidazole-1-carboxylic acid benzyl ester Dimethylformamide (25 mL) was added to 5,6-dichloro-2-(4-methoxy-3-nitro-phenyl)-1H-benzoimidazole (1.01 g, 3 mmol) from Step A. As the mixture stirred, sodium hydride (0.168 g, 4.2 mmol) was gradually added. After 3 hours, benzyl chloroformate (0.857 mL, 6 mmol) was added dropwise to the mixture. The reaction mixture was stirred overnight and then was partitioned between water (1,000 mL) and ethyl acetate (500 mL). The solvent was removed on the rotary evaporator and the residue triturated with 4:1 hexane:ethyl acetate to give the product (0.62 g), mp 212–214° C.

Calculated for $C_{22}H_{15}Cl_2N_3O_5 \cdot 0.23H_2O$: C, 55.46; H, 3.27; N, 8.82. Found: C, 55.49; H, 3.24; N, 8.89.

Step C: 2-(3-Amino-4-methoxy-phenyl)-5,6-dichloro-benzoimidazole-1-carboxylic acid benzyl ester 5,6-Dichloro-2-(4-methoxy-3-nitro-phenyl)-benzoimidazole-1-carboxylic acid benzyl ester (1.14 g, 2.4 mmol) from Step B was combined with glacial acetic acid (50 mL). Zinc dust (7.81 g, 120 mmol) was then gradually added to the stirred reaction mixture. After 2 hours, the zinc was filtered from the reaction mixture and the filtrate concentrated to an oil via rotary evaporation (60° C.). The oil was taken up in ethyl acetate and washed with saturated aqueous sodium bicarbonate solution and brine, dried (magnesium sulfate), filtered and the solvent removed. The solid was triturated with 7:3 hexane:ethyl acetate to give the product (0.6 g), mp 150–160° C.

Calculated for $C_{22}H_{17}Cl_2N_3O_3$: C, 59.74; H, 3.87; N, 9.50. Found: C, 59.47; H 3.91; N, 9.38.

Step D: 5,6-Dichloro-2-[4-methoxy-3-(thiophene-2-sulfonylamino)-phenyl]-benzoimidazole-1-carboxylic acid benzyl ester 2-(3-Amino-4-methoxy-phenyl)-5,6-dichloro-benzoimidazole-1-carboxylic acid benzyl ester from Step C was mixed with pyridine (5 mL) and 2-thienylsulfonyl chloride (0.1283 g, 0.7 mmol) was added. The mixture was allowed to stand overnight. Water (100 mL) was added to the reaction mixture and the product crystallized within 5 hours. The solid was then collected by filtration and triturated with 1/1, hexanes/ethyl acetate (0.2 g), mp 195–198° C.

Calculated for $C_{26}H_{19}Cl_2N_3O_5S_2$: C, 53.07; H, 3.25; N, 7.14. Found: C, 52.95; H, 3.23; N, 7.09.

EXAMPLE 11

3-{[5-(5,6-Difluoro-1H-indol-2-yl)-2-methoxy-phenylamino]-methyl}-phenol

3-Hydroxybenzaldehyde (0.2 g, 1.64 mmol) was added to a stirred mixture of 5-(5,6-difluoro-1H-indol-2-yl)-2-methoxy-phenylamine (0.45 g, 1.64 mmol) in methylene chloride (125 mL), followed by acetic acid (0.2 g, 3.33 mmol). The resulting mixture was stirred at room temperature for 1 hour. Sodium triacetoxyborohydride (0.35 g, 1.65 mmol) was added in one portion, and the resulting homogeneous solution stirred at room temperature for 3 days. Saturated aqueous sodium bicarbonate solution (100 mL) was added and the mixture stirred for 2 hours. The mixture was shaken and the organic layer separated. The solvent was evaporated to give a brown gum, recrystallization from methanol/water gave the product as white crystals (150 mg), mp 203–205° C.

Calculated for $_{22}H_{18}N_2O_2F_2$: C, 69.47; H, 4.77; N, 7.36. Found: C, 69.20; H, 4.90; N, 7.25.

EXAMPLE 12

[5-(5,6-Difluoro-1H-indol-2-yl)-2-methoxy-phenyl]-thiophen-2-ylmethyl-amine

2-Thiophenecarboxaldehyde (0.112 g, 1.0 mmol) was added to a stirred mixture of 5-(5,6-difluoro-1H-indol-2-yl)-2-methoxy-phenylamine (0.29 g, 1.06 mmol) in methylene chloride (125 mL), followed by acetic acid (0.1 g, 1.67 mmol). The resulting mixture was stirred at room temperature for 1 hour. Sodium triacetoxyborohydride (0.23 g, 1.09 mmol) was added in one portion, and the resulting homogeneous solution stirred at room temperature for 6 days. Saturated aqueous sodium bicarbonate solution (100 mL) was added and the mixture stirred for 2 hours. The mixture was shaken and the organic layer separated. The solvent was evaporated to give a brown gum. Recrystallization from methanol/water gave the product as a brown solid (120 mg), mp 190–192° C.

Calculated for $C_{20}H_{16}N_2OSF_2$: C, 64.85; H, 4.35; N, 7.56. Found: C, 64.70; H, 4.23; N, 7.26.

EXAMPLE 13

[5-(5,6-Difluoro-1H-indol-2-yl)-2-methoxy-phenyl]-(4-methoxy-benzyl)-amine

4-Methoxybenzaldehyde (0.204 g, 1.5 mmol) was added to a stirred mixture of 5-(5,6-difluoro-1H-indol-2-yl)-2-methoxy-phenylamine (0.405 g, 1.48 mmol) in methylene chloride (125 mL), followed by acetic acid (0.3 g, 1.5 mmol). The resulting mixture was stirred at room temperature for 1 hour. Sodium triacetoxyborohydride (0.31 g, 1.46 mmol) was added in one portion, and the resulting homogeneous solution stirred at room temperature for 3 days. Saturated aqueous sodium bicarbonate solution (100 mL) was added and the mixture stirred for 2 hours. The mixture was shaken, the organic layer separated and dried over $Na_2SO_4$. The solvent was evaporated to give a yellow oil. Recrystallization from methanol/water gave the product as off-white crystals (270 mg); mp 173–175° C.

Calculated for $C_{23}H_{20}N_2O_2F_2$: C, 70.04; H, 5.11; N, 7.10. Found: C, 70.19; H, 5.01; N, 7.12.

EXAMPLE 14

4-{[5-(5,6-Difluoro-1H-indol-2-yl)-2-methoxy-phenylamino]-methyl}-benzoic acid methyl ester Methyl 4-formylbenzoate (0.21 g, 1.28 mmol) was added to a stirred mixture of 5-(5,6-difluoro-1H-indol-2-yl)-2-methoxy-phenylamine (0.34 g, 1.24 mmol) in methylene chloride (125 mL), followed by acetic acid (0.3 g, 3.33 mmol). The resulting mixture was stirred at room temperature for 1 hour. Sodium triacetoxyborohydride (0.3 g, 1.42 mmol) was added in one portion, and the resulting homogeneous solution stirred at room temperature for 4 days. Saturated aqueous sodium bicarbonate solution (100 mL) was added and the mixture stirred for 2 hours. The mixture was shaken, the organic layer separated, and dried over $Na_2SO_4$. The solvent was evaporated to give a brown gum. Recrystallization from methanol gave the product as off-white crystals (140 mg), mp 168–170° C.

Calculated for $C_{24}H_{20}N_2O_3F_2$: C, 68.24; H, 4.77; N, 6.63. Found: C, 67.78; H, 4.63; N, 6.41.

EXAMPLE 15

N-[5-(5,6-Difluoro-1H-indol-2-yl)-2-methoxy-phenyl]-3-nitro-benzenesulfonamide

The product from Example 3, 5-(5,6-difluoro-1H-indol-2-yl)-2-methoxy-phenylamine (0.548 g, 2.0 mmol), was mixed with 3-nitrobenzenesulfonyl chloride (0.466 g, 2.0 mmol) and pyridine (9 mL) was added, and the reaction mixture was heated briefly to 50° C. and then allowed to stand overnight at room temperature. Water (15 mL) was added and the mixture allowed to stand 1.5 hours at room temperature. The mixture was partitioned between water (200 mL) and ethyl acetate (200 mL), and the organic layer was washed with 1N HCl (100 mL), water (100 mL), and brine (100 mL), dried (magnesium sulfate), filtered, and concentrated to a yellow solid. The solid was triturated with hexanes/ethyl acetate, 1/1, dried in vacuo, taken up in tetrahydrofuran, concentrated to dryness, triturated with hexanes/ethyl acetate, 4/1, v/v and was collected by filtration (0.488 g), mp 228–230° C.

Calculated for $C_{21}H_{15}F_2N_3O_5S$: C, 54.90; H, 3.29; N, 9.15. Found: C, 55.11; H, 3.66; N, 8.22.

EXAMPLE 16

3-Amino-N-[5-(5,6-difluoro-1H-indol-2-yl)-2-methoxy-phenyl]-benzenesulfonamide

The product from Example 15 (0.388 g, 0.84 mmol) was taken up in glacial acetic acid (25 mL), and zinc dust (2.8 g, 325 mesh) was added in portions over 3 minutes and was then stirred 2 hours at room temperature. The zinc was filtered off and washed with ethyl acetate and tetrahydrofuran. The organic solution was concentrated to dryness, the residue partitioned between ethyl acetate (200 mL) and sodium bicarbonate solution (200 mL), the organic layer washed with brine and dried (magnesium sulfate), filtered, concentrated, and the resulting solid triturated with hexanes/ethyl acetate, 3/1, v/v and the insoluble portion collected by filtration to give the product as a faintly yellow solid (0.296 g), mp 235–238° C.

Calculated for $C_{21}H_{17}F_2N_3O_3S$: C, 58.73; H, 3.99; N, 9.78. Found: C, 58.71; H, 3.98; N, 9.44.

EXAMPLE 17

4-{3-[5-(1H-Indol-2-yl)-2-methoxy-phenyl]-thioureido}-benzenesulfonamide

The product from Example 1, Step B, 5-(1H-indol-2-yl)-2-methoxy-phenylamine (0.12 g, 0.1 mmol) was reacted with 4-isothiocyanatobenzene sulfonamide (0.108 g, 0.1 mmol) according to the procedure for Example 2 to give the product (0.14 g).

Calculated for $C_{22}H_{20}N_4O_2S_2$: C, 58.39; H, 4.45; N, 12.38. Found: C, 57.85; H, 4.36; N, 12.04.

EXAMPLE 18

5-(5,6-Dichloro-1H-indol-2-yl)-2-methoxy-phenylamine

Step A: 3,4-Dichlorophenylacetyl chloride 3,4-Dichlorophenylacetyl chloride was prepared from 3,4-dichlorophenylacetic acid (32.20 g, 0.157 mol) according to the procedure for Example 3, Step A to give the product which was used directly in the next step.

Step B: 4-Methoxyphenyl-3',4'-dichlorobenzyl ketone

4-Methoxyphenyl-3',4'-dichlorobenzyl ketone was prepared according to the procedure for Example 3, Step B to give the product as a white solid (40.18 g), mp 107–108° C.

Step C: 2-(4,5-Dichloro-2-nitro-phenyl)-1-(4-methoxy-3-nitro-phenyl)-ethanone 2-(4,5-Dichloro-2-nitro-phenyl)-1-(4-methoxy-3-nitro-phenyl)-ethanone was prepared from 4-methoxyphenyl-3',4'-dichlorobenzyl ketone (15.2 g, 51 mmol) according to the procedure for Example 3, Step C to give the product as a white solid (6.26 g), mp 203–204° C.

Calculated for $C_{15}H_{10}Cl_2N_2O_6$: C, 46.78; H, 2.62; N, 7.27. Found: C, 46.42; H, 2.73; N, 7.22.

Step D: 5-(5,6-Dichloro-1H-indol-2-yl)-2-methoxy-phenylamine 5-(5,6-Dichloro-1H-indol-2-yl)-2-methoxy-phenylamine was prepared from 2-(4,5-dichloro-2-nitro-phenyl)-1-(4-methoxy-3-nitro-phenyl)-ethanone (5.91 g, 15.3 mmol) according to the procedure for Example 3, Step D to give the product as a tan solid (1.25 g), mp 235–237° C.

Calculated for $C_{15}H_{12}Cl_2N_2O$: C, 58.65; H, 3.94; N, 9.12. Found: C, 58.92; H, 3.97; N, 9.01.

EXAMPLE 19

3-{3-[5-(5,6-Dichloro-1H-indol-2-yl)-2-methoxy-phenyl]-thioureido}-benzoic acid

3-{3-[5-(5,6-Dichloro-1H-indol-2-yl)-2-methoxy-phenyl]-thioureido}-benzoic acid was prepared from the product of Example 18, Step D, 5-(5,6-dichloro-1H-indol-2-yl)-2-methoxy-phenylamine (0.64 g, 1.72 mmol) and 3-carboxyphenyl isothiocyanate (0.359 g, 2.0 mmol) to give the product as a reddish-tan solid (0.104 g), mp 216–218° C.

Calculated for $C_{23}H_{17}Cl_2N_3O_3S$: C, 56.80; H, 3.52; N, 8.64. Found: C, 55.92; H, 3.72; N, 8.33.

EXAMPLE 20

Dodecane-1-sulfonic acid [5-(5,6-difluoro-1H-indol-2-yl)-methoxy-phenyl]-amide

1-Dodecanesulfonyl chloride (0.3 g, 1.1 mmol) was added to a stirred solution of 5-(5,6-difluoro-1H-indol-2-yl)-2-methoxy-phenyl-amine from Example 3 (0.3 g, 1.11 mmol) in pyridine (3 mL) under an inert atmosphere at room temperature. After approximately 20 hours the mixture was poured into water (30 mL), stirred, and acidified with aqueous HCl. After several hours the precipitate was filtered off, rinsed three times with water, and dried. Recrystallization from ethanol afforded the product (0.25 g), mp 148–149° C.

Calculated for $C_{27}H_{36}F_2N_2O_3S$: C, 64.01; H, 7.16; N, 5.53. Found: C, 62.95; H, 6.92; N, 5.34.

EXAMPLE 21

Dodecane-1-sulfonic acid [5-(5,6-dichloro-1H-benzoimidazol-2-yl)-2-methoxy-phenyl]-amide Step A: 5,6-Dichloro-2-(4-methoxy-3-nitro-phenyl)-1H-benzoimidazole 4-Methoxy-3-nitrobenzaldehyde (4.65 g, 27.6 mmol) and sodium bisulfite (5.79 g, 55.2 mmol) were added to ethanol (200 mL) and refluxed for 4 hours at which time, 1,2-dichloro-4,5-phenylenediamine (4.56 g, 27.6 mmol) was added and the mixture was refluxed overnight. The reaction mixture was filtered while hot and the pea-green solid washed with ethanol (3.09 g), mp>250° C.

Calculated for $C_{14}H_9Cl_2N_3O_3$: C, 49.73; H, 2.68; N, 12.43. Found: C, 49.61; H, 2.81; N, 12.26.

Step B: 5-(5,6-Dichloro-1H-benzoimidazol-2-yl)-2-methoxy-phenylamine

The product from Step A (3.09 g, 9.14 mmol) was added to glacial acetic acid (250 mL). Zinc (21.68 g, 331.7 mmol) was gradually added with stirring. After stirring 1.5 hours, zinc was filtered from the mixture and the solution was concentrated to a dark oil. Methylene chloride (100 mL) was added to the oil and the desired product crystallized out overnight (0.3154 g), mp>300° C.

Calculated for $C_{14}H_{11}Cl_2N_3O \cdot \frac{1}{6}C_2H_4O_2 \cdot \frac{7}{10}H_2O$: C, 52.05; H, 3.88; N, 12.71. Found: C, 52.01; H, 3.48; N, 12.59.

Step C: Dodecane-1-sulfonic acid [5-(5,6-dichloro-1H-benzoimidazol-2-yl -2-methoxy-phenyl]-amide 1-Dodecanesulfonyl chloride (0.38 g, 1.4 mmol) was added to a stirred suspension of 5-(5,6-dichloro-1H-benzoimidazol-2-yl)-2-methoxy-phenylamine from Step B (0.6 g, 1.4 mmol) in pyridine (6 mL) under an inert atmosphere, warmed briefly to 80° C. then stirred at room temperature. After approximately 20 hours the mixture was poured into water (60 mL), stirred, and acidified with aqueous HCl. After several hours the mixture was extracted with dichloromethane (60 mL, 30 mL) and the combined extracts were washed with water then 0.5 M sodium bicarbonate solution. A little saturated brine was added to assist with stratification. The organic phase was washed with saturated brine, dried over $MgSO_4$, and stripped of solvent to leave the crude product as a crystalline residue. Recrystallization from acetonitrile followed by chromatography on silicagel in $CHCl_3$/EtOAc (9:1) afforded the product (0.03 g), mp 203–204° C.

Calculated for $C_{26}H_{35}Cl_2N_3O_3S$: C, 57.77; H, 6.53; N, 7.77. Found: C, 57.19; H, 6.27; N, 7.45.

EXAMPLE 22

[5-(5,6-Difluoro-1H-indol-2-yl)-2-methoxy-phenyl]-(3-trifluoro-methylphenyl)-amine A mixture of 5-(5,6-difluoro-1H-indol-2-yl)-2-methoxy-phenylamine from Example 3 (0.5 g, 1.8 mmol), tris(3-trifluoro-methylphenyl)bismuthane (1.3 g, 2.0 mmol), copper(II) acetate (0.35 g, 1.9 mmol), and triethylamine (0.19 g, 1.9 mmol) was stirred under an inert atmosphere in dichloromethane (50 mL) and heated to reflux. After 24 hours, the mixture was allowed to cool and was then diluted with additional dichloromethane (25 mL) and stirred into 2N hydrochloric acid (250 mL). After 2 hours, the layers were separated and the organic phase washed successively with 2N HCl, water, 0.5 M aqueous potassium carbonate, water, and saturated aqueous sodium chloride, then dried over $MgSO_4$. The solution was filtered then stripped of solvent under reduced pressure to afford a solid residue which was recrystallized from toluene/hexane (1:1) then purified by chromatography on a column of silicagel in chloroform to give the product (0.7 g), mp 144–146° C.

Calculated for $C_{22}H_{15}F_5N_2O$: C, 63.16; H, 3.61; N, 6.70. Found: C, 62.46; H, 3.64; N, 6.32.

EXAMPLE 23

(4-{3-[5-(1H-Indol-2-yl)-2-methoxy-phenyl]-thioureido}-benzyl)-phosphonic acid diethyl ester Step A: Diethyl 4-isothiocyanatobenzylphosphonate Thiophosgene (4.1 mL, 54 mmol) was added al at once to a mixture of diethyl 4-aminobenzylphosphonate (12.04 g, 50 mmol), sodium bicarbonate (8.33 g, 99 mmol), water (100 mL), and dichloromethane (250 mL), and the mixture was stirred at room temperature for about 2 hours. The organic and aqueous layers were separated, the organic layer dried over magnesium sulfate, filtered, and concentrated to give the product isothiocyanate as a brown oil. This was used directly in the next step.

Step B: 4-{3-[5-(1H-Indol-2-yl)-2-methoxy-phenyl]-thioureido}-benzyl)-phosphonic acid diethyl ester The product from Example 1 (0.119 g, 0.5 mmol) and the product from Example 23, Step A (0.157 g, 0.54 mmol) were combined in tetrahydrofuran (8 mL), briefly heated to 50° C., and then allowed to stand for 6 hours at room temperature. The reaction mixture was concentrated to dryness and the residue triturated with hexanes/ethyl acetate. The product was collected by filtration (0.14 g), mp softening at 120° C., gradual decomposition.

Calculated for $C_{27}H_{30}N_3O_4PS \cdot 0.33\ C_4H_8O_2$: C, 61.54; H, 5.95; N, 7.60. Found: C, 61.30; H, 6.03; N, 7.34.

EXAMPLE 24

(4-{3-[5-(5,6-Difluoro-1H-indol-2-yl)-2-methoxy-phenyl]-thioureido}-benzyl)-phosphonic acid diethyl ester The product from Example 3, 5-(5,6-difluoro-1H-indol-2-yl)-2-methoxy-phenylamine, (0.137 g, 0.5 mmol) was reacted with the product from Example 23, Step A (0.156 g, 0.54 mmol) according to the procedure for Example 23, Step B to give the product (0.172 g), mp 180–182° C.

Calculated for $C_{27}H_{28}F_2N_3O_4PS$: C, 57.95; H, 5.04; N, 7.51. Found: C, 57.30; H, 4.94; N, 7.34.

EXAMPLE 25

1-(3,5-Dichloro-phenyl)-3-[5-(5,6-difluoro-1H-indol-2-yl)-2-methoxy-phenyl]-urea The product from Example 3, 5-(5,6-difluoro-1H-indol-2-yl)-2-methoxy-phenylamine (0.266 g, 0.97 mmol), was reacted with 3,5-dichlorophenyl isocyanate (0.206 g, 1.1 mmol) in ethyl acetate (8 mL) overnight at room temperature. The reaction mixture was concentrated to dryness and triturated with hexanes/ethyl acetate and the solid collected by filtration. The solid was filtered through silica gel using tetrahydrofuran as eluant. The product-containing fractions were concentrated and triturated with dichloromethane and the product was collected as a solid (0.181 g), mp 240–243° C.

Calculated for $C_{22}H_{15}Cl_2F_2N_3O_2 \cdot 0.16\ CH_2Cl_2$: C, 55.77; H, 3.45; N, 8.80. Found: C, 55.46; H, 3.30; N, 8.60.

EXAMPLE 26

[5-(1H-Indol-2-yl)-2-methoxy-phenyl]-thiourea

Step A: [5-(1H-Indol-2-yl)-2-methoxy-phenyl]-isothiocyanate

The product from Example 1, 5-(1H-indol-2-yl)-2-methoxy-phenylamine, (4.76 g, 20 mmol) was reacted with thiophosgene (1.9 mL, 25 mmol) according to the procedure for Example 23, Step A, to give [5-(1H-indol-2-yl)-2-methoxy-phenyl]-isothiocyanate (4.55 g), as a black solid.

Step B: [5-(1H-Indol-2-yl)-2-methoxy-phenyl]-thiourea

The product from Step A, [5-(1H-indol-2-yl)-2-methoxy-phenyl]-isothiocyanate, (0.146 g, 0.52 mmol) was added to aqueous ammonia (50 mL). Tetrahydrofuran (10 mL) was added and the mixture was stirred 3 hours at room temperature, diluted with ethyl acetate (100 mL), the layers were separated, the organic layer dried, filtered, and concentrated. The residue was triturated with hexanes/ethyl acetate to give the product (0.096 g), mp 188–191° C.

Calculated for $C_{16}H_{15}N_3OS \cdot 0.5\ H_2O$: C, 62.72; H, 5.26; N, 13.71. Found: C, 62.95; H, 5.08; N, 13.48.

EXAMPLE 27

(R)-1-[5-(1H-Indol-2-yl)-2-methoxy-phenyl]-3(1-phenyl-ethyl)-thiourea

The product from Example 26, Step A, [5-(1H-indol-2-yl)-2-methoxy-phenyl]-isothiocyanate, (0.142 g, 0.51 mmol) was reacted with R-α-methylbenzyl amine (0.068 g, 0.56 mmol) according to the procedure for Example 23, Step B to give 0.148 g of a solid. The solid was filtered through silica gel using hexanes/ethyl acetate, 1/1, v/v as eluant The product-containing fractions were concentrated and triturated with hexanes/ethyl acetate, 4/1, to give the product as a light tan solid (0.046 g), mp 179–181° C.

Calculated for $C_{24}H_{23}N_3OS$: C, 71.79; H, 5.77; N, 10.46. Found: C, 72.59; H, 5.85; N, 10.32.

EXAMPLE 28

3Cyano-N-[5-(5,6-difluoro-1H-indol-2-yl)-2-methoxy-phenyl]-benzenesulfonamide

The product from Example 3, 5-(5,6-difluoro-1H-indol-2-yl)-2-methoxy-phenylamine, (0.274 g, 1.0 mmol) was mixed with 3cyanobenzenesulfonyl chloride (0.208 g, 1.0 mmol) and pyridine (4 mL) was added and the reaction mixture was agitated by hand and the allowed to stand overnight at room temperature. The reaction mixture was added to water (45 mL) and allowed to stand overnight at room temperature. A solid had formed and was collected by filtration. The solid was slurried in ethyl acetate. The insoluble material was taken up in tetrahydrofuran, concentrated, and triturated with ethyl acetate. The product was collected by filtration (0.318 g), mp 239–242° C.

Calculated for $C_{22}H_{15}F_2N_3O_3S \cdot 0.5\ H_2O$: C, 58.92; H, 3.60; N, 9.37. Found: C, 59.25; H, 3.41; N, 9.07.

EXAMPLE 29

[5-(1H-Indol-2-yl)-2-methoxy-phenyl]-methyl-amine

In acetone (50 mL) was placed 5-(1H-indol-2-yl)-2-methoxy-phenylamine (2.38 g, 10 mmol). To this was added potassium carbonate (5.53 g, 40 mmol), and to the vigorously stirred mixture was added methyl iodide (1.55 g, 11 mmol). The mixture warmed to 40° C. and stirred for 48 hours. The mixture cooled to room temperature and was filtered free of inorganics. The resulting solution was evaporated in vacuo to give a solid which was partitioned between ethyl acetate (50 mL) and water (50 mL). The organic phase was separated, dried over magnesium sulfate, and evaporated in vacuo to give a tan solid. This solid was purified by flash chromatography over silica gel (5% ethyl acetate/methylene chloride). Evaporation of the appropriate fractions gave 0.68 g of pure compound. MS: M+1=253.1. $^1$H NMR (DMSO-d$_6$) δ 2.79 (d, J=5.3 Hz, 3H), 3.80 (s, 3H), 5.08–5.12 (m, 1H), 6.69 (s, 1H), 6.83–7.05 (m, 5H), 7.33 (d, J=7.9 Hz, 1H), 7.44 (d, J=8.0 Hz, 1H), 11.28 (s, 1H) ppm.

Calculated for $C_{16}H_{16}N_2O$: C, 76.16; H, 6.39; N, 11.10. Found: C, 76.03; H, 6.45; N, 11.12.

EXAMPLE 30

5-{3-[5-(5,6-Difluoro-1H-indol-2-yl)-2-methoxy-phenyl]-thioureido}-isophthalic acid Step A: 3,5-Dicarboxyphenyl isothiocyanate 5-Aminoisophthalic acid (3.62 g, 20 mmol) was reacted according to the procedure for Example 23, Step A, except that the reaction mixture was heated until the orange color disappeared. The resulting gelatinous suspension was filtered and then partitioned between ethyl acetate and water. The organic layer was dried over magnesium sulfate, filtered and concentrated to give a white solid (0.79 g). This was used directly in the next step.

Step B: 5-{3-[5-(5,6-Difluoro-1H-indol-2-yl)-2-methoxy-phenyl]-thioureido}-isophthalic acid The product from Example 3, 5-(5,6-difluoro-1H-indol-2-yl)-2-methoxy-phenylamine, (0.152 g, 0.55 mmol) was reacted with the product from Step A, 3,5-dicarboxyphenyl isothiocyanate (0.120 g, 0.53 mmol) in tetrahydrofuran (7 mL). The reaction mixture was heated until all solids dissolved and then was allowed to stand overnight at room temperature. The reaction mixture was concentrated and triturated with ethyl acetate and the product collected by filtration (0.208 g), mp (slow decomposition over a wide temperature range).

Calculated for $C_{24}H_{17}F_2N_3O_5S \cdot 0.5\ H_2O \cdot 0.5\ C_4H_8O_2$: C, 56.72; H, 4.03; N, 7.63. Found: C, 56.79; H, 4.08; N, 7.20.

EXAMPLE 31

(2-{3-[5-(1H-Indol-2-yl)-2-methoxy-phenyl]-thioureido}-ethyl)-carbamic acid tert-butyl ester The product from Example 26, Step A, [5-(1H-indol-2-yl)-2-methoxy-phenyl]-isothiocyanate, (0.272 g, 1.0 mmol) and mono-tert-butyloxycarbonyl ethylenediamine (0.156 g, 1.0 mmol) were heated briefly to 50° C. in ethyl acetate (20 mL). The reaction mixture was allowed to stand 1 hour at room temperature and was then concentrated. The residue was filtered through silica gel using hexanes/ethyl acetate as eluant The purest product-containing factions were combined, concentrated, and triturated with 3/1, hexanes/ethyl acetate, v/v, to give the product as an off-white solid (0.09 g), mp 159–160° C.

Calculated for $C_{23}H_{28}N_4O_3S$: C, 62.70; H, 6.41; N, 12.72. Found: C, 61.73; H, 6.34; N, 12.44.

EXAMPLE 32

4-{3-[5-(1H-Indol-2-yl)-2-methoxy-phenyl]-thioureido}-benzoic acid

The product from Example 1, Step B, 5-(1H-indol-2-yl)-2-methoxy-phenylamine (0.286 g, 1.0 mmol) was mixed with 4-carboxyphenyl isothiocyanate (0.185 g, 1.03 mmol) in tetrahydrofuran (40 mL). The solvent was boiled off on the rotary evaporator (no vacuum), and ethyl acetate was added to the residue and the insoluble material was collected by filtration. The collected solid was taken up in tetrahydrofuran, concentrated to dryness, and triturated again with ethyl acetate to give the product as a white solid (0.180 g), mp 201–203° C.

Calculated for $C_{23}H_{19}N_3O_3S \cdot 0.25\ C_4H_8O_2$: C, 65.59; H, 4.82; N, 9.56. Found: C, 65.19; H, 4.63; N, 9.78.

EXAMPLE 33

(3-{3-[5-(1H-Indol-2-yl)-2-methoxy-phenyl]-thioureido}-phenyl)-acetic acid

The product from Example 26, Step A, [5-(1H-indol-2-yl)-2-methoxy-phenyl]-isothiocyanate (0.211 g, 0.75 mmol) and 3-aminophenylacetic acid (0.118 g, 0.78 mmol) in tetrahydrofuran (20 mL) were briefly heated to 50° C. and then allowed to stand 3 days at room temperature. The solvent was boiled off and the residue triturated with hexanes/ethyl acetate, 3/1, v/v. The solid was collected by filtration and was then filtered through silica gel using tetrahydrofuran as eluant. The purest fractions were combined, concentrated, and triturated with hexanes/ethyl acetate, 3/1, v/v. The product was collected as a yellow solid (0.040 g), mp 174–175° C.

Calculated for $C_{24}H_{21}N_3O_3S \cdot 0.50\ H_2O$: C, 65.44; H, 5.03; N, 9.54. Found: C, 65.88; H, 4.95; N, 9.28.

EXAMPLE 34

(4-{3-[5-(1H-Indol-2-yl)-2-methoxy-phenyl]-thioureido}-phenyl)-acetic acid

The product from Example 26, Step A, [5-(1H-indol-2-yl)-2-methoxy-phenyl]-isothiocyanate (0.210 g, 0.75 mmol) and 4-aminophenylacetic acid (0.115 g, 0.76 mmol) in tetrahydrofuran (20 mL) were briefly heated to 50° C. and then allowed to stand 3 days at room temperature. The solvent was boiled off and the residue triturated with hexanes/ethyl acetate, 3/1, v/v. The solid was collected by filtration and was then washed with methylene chloride/methanol, 9/1, v/v. The product was obtained as a faintly yellow solid (0.099 g), mp 190–192° C.

Calculated for $C_{24}H_{21}N_3O_3S \cdot 0.50\ H_2O$: C, 65.44; H, 5.03; N, 9.54. Found: C, 65.58; H, 4.93; N, 9.43.

EXAMPLE 35

1-[5-(5,6-Difluoro-1H-indol-2-yl)-2-methoxy-phenyl]-3-((S)-1-phenyl-ethyl)-thiourea Step A: 5-(5,6-Difluoro-1H-indol-2-yl)-2-methoxy-phenyl isothiocyanate The product from Example 3, 5-(5,6-difluoro-1H-indol-2-yl)-2-methoxy-phenylamine (5.48 g, 20 mmol) was reacted with thiophosgene (1.9 mL, 25 mmol) according to the procedure for Example 26, Step A to give the product as a greenish tan solid (5.40 g).

Step B: -[5-(5,6-Difluoro-1H-indol-2-yl)-2-methoxy-phenyl]-3-((S)-1-phenyl-ethyl)-thiourea The product from Step A, 5-(5,6-difluoro-1H-indol-2-yl)-2-methoxy-phenyl isothiocyanate (0.316 g, 1.0 mmol) was reacted with S-α-methylbenzylamine (0.128 g, 1.06 mmol) according to the procedure for Example 23, Step B to give the product after filtration through silica gel using hexanes/ethyl acetate, 1/1, v/v as eluant (0.393 g in 2 portions), mp 102–106° C.

Calculated for $C_{24}H_{21}F_2N_3OS \cdot 0.25\ C_4H_8O_2$: C, 65.34; H, 5.04; N, 9.14. Found: C, 65.05; H, 5.12; N, 8.85.

EXAMPLE 36

(S)-3-tert-Butoxy-2-{3-[5-(5,6-Difluoro-1H-indol-2-yl)-2-methoxy-phenyl]-thioureido}-propionic acid tert-butyl ester The product from Example 35, Step A, 5-(5,6-difluoro-1H-indol-2-yl)-2-methoxy-phenyl isothiocyanate (0.316 g, 1.0 mmol) was reacted with serine tert-butylether tert-butylester (0.226 g, 1.0 mmol) according to the procedure for Example 23, Step B to give the product after filtration through silica gel using hexanes/ethyl acetate, 1/1, v/v as eluant (0.377 g in 2 portions), mp 111–114° C.

Calculated for $C_{27}H_{33}F_2N_3O_4S$: C, 60.77; H, 6.23; N, 7.87. Found: C, 61.14; H, 6.49; N, 7.50.

EXAMPLE 37

1-[5-(5,6-Difluoro-1H-indol-2-yl)-2-methoxy-phenyl]-3-(2-hydroxy-ethyl)-thiourea The product from Example 35, Step A, 5-(5,6-difluoro-1H-indol-2-yl)-2-methoxy-phenyl isothiocyanate (0.316 g, 1.0 mmol) was reacted with ethanolamine (0.082 g, 1.34 mmol) according to the procedure for Example 23, Step B to give the product as a light tan/yellow solid after trituration with ethyl acetate (0.324 g), mp 191–193° C.

Calculated for $C_{24}H_{17}F_2N_3O_5S \cdot 0.5\ H_2O$: C, 55.95; H, 4.70; N, 10.87. Found: C, 56.23; H, 4.65; N, 10.95.

EXAMPLE 38

(2-{3-[5-(5,6-Difluoro-1H-indol-2-yl)-2-methoxy-phenyl]-thioureido}-ethyl)-carbamic acid tert-butyl ester The product from Example 35, Step A, 5-(5,6-difluoro-1H-indol-2-yl)-2-methoxy-phenyl isothiocyanate (0.316 g, 1.0 mmol) was reacted with mono-tert-butyloxycarbonyl ethylenediamine (0.176 g, 1.2 mmol) according to the procedure for Example 23, Step B to give the product as an off-white solid after trituration with hexanes/ethyl acetate (0.392 g), mp 110–113° C.

Calculated for $C_{23}H_{26}F_2N_4O_3S$: C, 57.97; H, 5.50; N, 11.76. Found: C, 57.71; H, 5.88; N, 10.88.

EXAMPLE 39

1-[5-(5,6-Difluoro-1H-indol-2-yl)-2-methoxy-phenyl]-3-(3,4-difluoro-phenyl)-thiourea The product from Example 35, Step A, 5-(5,6-difluoro-1H-indol-2-yl)-2-methoxy-phenyl isothiocyanate (0.159 g, 0.5 mmol) was reacted with 3,4-difluoroaniline (0.068 g, 0.53 mmol) according to the procedure for Example 23, Step B to give the product as a solid after trituration with hexanes/ethyl acetate. Treatment of this solid with a second portion of 3,4-difluoroaniline (0.1 mL) at 50° C., and trituration with hexanes gave the product as a yellow solid (0.189 g), mp 183–186° C.

Calculated for $C_{22}H_{15}F_4N_3OS$: C, 59.32; H, 3.39; N, 9.43. Found: C, 58.98; H, 3.52; N, 9.17.

EXAMPLE 40

1-[5-(5,6-Difluoro-1H-indol-2-yl)-2-methoxy-phenyl]-3-((1S,2S)-2-hydroxy-1-hydroxymethyl-2-phenyl-ethyl)-thiourea The product from Example 35, Step A, 5-(5,6-difluoro-1H-indol-2-yl)-2-methoxy-phenyl isothiocyanate (0.316 g, 1.0 mmol) was reacted with (1S,2S)-(+)-2-amino-1-phenyl-1,3-propanediol (0.167 g, 1.0 mmol) according to the procedure for Example 23, Step B to give the product after trituration with hexanes/ethyl acetate, 1/1, v/v and filtration through silica gel using hexanes/ethyl acetate, 1/1, v/v as eluant The resulting orange oil/foam was triturated with hexanes/ether to give the product as an orange solid (0.155 g), mp (slow decomposition).

Calculated for $C_{25}H_{23}F_2N_3O_3S \cdot 0.25\ C_4H_{10}O$: C, 62.20; H, 5.12; N, 8.37. Found: C, 61.83; H, 5.47; N, 7.95.

EXAMPLE 41

1-[5-(5,6-Difluoro-1H-indol-2-yl)-2-methoxy-phenyl]-3-pyridin-3-yl-thiourea

The product from Example 3, 5-(5,6-difluoro-1H-indol-2-yl)-2-methoxy-phenylamine (0.277 g, 1.0 mmol) was mixed with 3-isothiocyanatopyridine (0.146 g, 1.07 mmol) in tetrahydrofuran (10 mL) and was heated briefly to 50° C. and then allowed to stand overnight at room temperature. The tetrahydrofuran was removed on the rotary evaporator to give a solid. The solid was triturated with hexanes/ethyl acetate, 1/1, v/v and was triturated a second time with hexanes/ethyl acetate, 4/1, v/v to give the product (0.309 g), mp 128–130° C.

Calculated for $C_{21}H_{16}F_2N_4O_3S \cdot 0.33\ C_4H_8O_2$: C, 61.00; H, 4.28; N, 12.74. Found: C, 60.75; H, 4.33; N, 12.58.

EXAMPLE 42

[5-(1H-indol-2-yl)-2-methoxy-phenyl]-(3-nitro-benzyl)-amine

3-Nitrobenzaldehyde (0.302 g, 2.0 mmol) was added to a stirred mixture of 5-(1H-indol-2-yl)-2-methoxy-phenylamine (0.476 g, 2.0 mmol) in methylene chloride (125 mL), followed by acetic acid (0.2 g). The resulting mixture was stirred at room temperature for 1 hour. Sodium triacetoxyborohydride (0.46 g, 2.2 mmol) was added in one portion, and the resulting homogeneous solution was stirred at room temperature for 3 days. Saturated aqueous sodium bicarbonate solution (100 mL) was added and the mixture was stirred for 2 hours. The mixture was shaken, the organic layer was separated and dried over $Na_2SO_4$. The solvent was evaporated to give an orange oil. Recrystallization from ethyl acetate/hexane gave the product (115 mg), mp 160–162° C.

Calculated for $C_{22}H_{19}N_3O_3$: C, 70.76; H, 5.13; N, 11.25. Found: C, 70.47; H, 5.32; N, 10.97.

EXAMPLE 43

[5-(1H-Indol-2-yl)-2-methoxy-phenyl]-(4-nitro-benzyl)-amine

4-Nitrobenzaldehyde (0.302 g, 2.0 mmol) was added to a stirred mixture of 5-(1H-indol-2-yl)-2-methoxy-phenylamine (0.476 g, 2.0 mmol) in methylene chloride (125 mL), followed by acetic acid (0.2 g). The resulting mixture was stirred at room temperature for 1 hour. Sodium triacetoxyborohydride (0.46 g, 2.2 mmol) was added in one portion, and the resulting homogeneous solution was stirred at room temperature for 4 days. Saturated aqueous sodium bicarbonate solution (100 mL) was added and the mixture was stirred for 2 hours. The mixture was shaken, the organic layer was separated and dried over $Na_2SO_4$. The solvent was evaporated to give an orange solid. Recrystallization from ethyl acetate gave the product (290 mg), mp 198–199° C.

Calculated for $C_{22}H_{19}N_3O_3$: C, 70.76; H, 5.13; N, 11.25. Found: C, 70.59; H, 5.05; N, 11.14.

EXAMPLE 44

[5-(1H-Indol-2-yl)-2-methoxy-phenyl]-(3-hydroxy-4-nitro-benzyl)-amine

3-Hydroxy-4-nitrobenzaldehyde (0.334 g, 2.0 mmol) was added to a stirred mixture of 5-(1H-indol-2-yl)-2-methoxy-phenylamine (0.476 g, 2.0 mmol) in methylene chloride (125 mL), followed by acetic acid (0.2 g). The resulting mixture is stirred at room temperature for 1 hour. Sodium triacetoxyborohydride (0.46 g, 2.2 mmol) was added in one portion, and the resulting homogeneous solution was stirred at room temperature for 3 days. Saturated aqueous sodium bicarbonate solution (100 mL) was added and the mixture is stirred for 2 hours. The mixture was shaken, the organic layer was separated and dried over $Na_2SO_4$. The solvent was evaporated to give a brown gum. Recrystallization from methanol gave the product (500 mg), mp 134–135° C.

Calculated for $C_{22}H_{19}N_3O_4$: C, 67.86; H, 4.92; N, 10.79. Found: C, 67.88; H, 5.01; N, 10.87.

EXAMPLE 45

[5-(1H-Indol-2-yl)-2-methoxy-phenyl]-(4-hydroxy-3-nitro-benzyl)-amine

4-Hydroxy-3-nitrobenzaldehyde (0.334 g, 2.0 mmol) was added to a stirred mixture of 5-(1H-indol-2-yl)-2-methoxy-phenylamine (0.476 g, 2.0 mmol) in methylene chloride (125 mL), followed by acetic acid (0.2 g). The resulting mixture was stirred at room temperature for 1 hour. Sodium triacetoxyborohydride (0.46 g, 2.2 mmol) was added in one portion, and the resulting homogeneous solution was stirred at room temperature for 3 days. Saturoted aqueous sodium bicarbonate solution (100 mL) was added and the mixture was stirred for 2 hours. The mixture was shaken, the organic layer was separated and dried over $Na_2SO_4$. The solvent was evaporated to give a brown gum. Recrystallization from methanol gave the product (307 mg), mp 165–166° C.

Calculated for $C_{22}H_{19}N_3O_4$: C, 67.86; H, 4.92; N, 10.79. Found: C, 67.37; H,5.16; N, 10.59.

EXAMPLE 46

[5-(5,6-Difluoro-1H-indol-2-yl)-2-methoxy-phenyl]-(3-nitro-benzyl)-amine

3-Nitrobenzaldehyde (0.3 g, 2.0 mmol) was added to a stirred mixture of 5-(5,6-difluoro-1H-indol-2-yl)-2-methoxy-phenylamine (0.548 g, 2.0 mmol) in methylene chloride (125 mL), followed by acetic acid (0.2 g). The resulting mixture is stirred at room temperature for 1 hour. Sodium triacetoxyborohydride (0.46 g, 2.2 mmol) was added in one portion, and the resulting homogeneous solution was stirred at room temperature for 6 days. Saturated aqueous sodium bicarbonate solution (100 mL) was added and the mixture was sired for 2 hours. The mixture was shaken, the organic layer was separated and dried over $Na_2SO_4$. The solvent was evaporated to give a yellow solid. Recrystallization from methanol gave the product (220 mg), mp 212–214° C.

Calculated for $C_{22}H_{17}N_3O_3F_2$: C, 64.55; H, 4.19; N, 10.26. Found: C, 64.61; H, 4.14; N, 10.20.

EXAMPLE 47

[5-(5,6-Difluoro-1H-indol-2-yl)-2-methoxy-phenyl]-(4nitro-benzyl)-amine

4-Nitrobenzaldehyde (0.3 g, 2.0 mmol) was added to a stirred mixture of 5-(5,6-difluoro-1H-indol-2-yl)-2-methoxy-phenylamine (0.548 g, 2.0 mmol) in methylene chloride (125 mL), followed by acetic acid (0.2 g). The resulting mixture was stirred at room temperature for 1 hour. Sodium triacetoxyborohydride (0.46 g, 2.2 mmol) was added in one portion, and the resulting homogeneous solution was stirred at room temperature for 6 days. Saturated aqueous sodium bicarbonate solution (100 mL) was added, and the mixture was stirred for 2 hours. The mixture was shaken; the organic layer was separated and dried over $Na_2SO_4$. The solvent was evaporated to give a red solid. Recrystallization from methanol gave the product (450 mg), mp 181–182° C.

Calculated for $C_{22}H_{17}N_3O_3F_2$: C, 64.55; H, 4.19; N, 10.26. Found: C, 64.45; H, 4.36; N, 10.27.

EXAMPLE 48

[5-(5,6-Difluoro-1H-indol-2-yl)-2-methoxy-phenyl]-(3-hydroxy-4-nitro-benzyl)-amine 3-Hydroxy-4-nitrobenzaldehyde (0.334 g, 2.0 mmol) was added to a stirred mixture of 5-(5,6-difluoro-1H-indol-2-yl)-

2-methoxy-phenylamine (0.548 g, 2.0 mmol) in methylene chloride (125 mL), followed by acetic acid (0.2 g). The resulting mixture was stirred at room temperature for 1 hour. Sodium triacetoxyborohydride (0.46 g, 2.2 mmol) was added in one portion, and the resulting homogeneous solution was stirred at room temperature for 3 days. Saturated aqueous sodium bicarbonate solution (100 mL), was added and the mixture was stirred for 2 hours. The mixture was shaken; the organic layer was separated and dried over $Na_2SO_4$. The solvent was evaporated to give a red-orange gum. Recrystallization from methanol gave the product (350 mg), mp 170–171° C.

Calculated for $C_{22}H_{17}N_3O_4F_2$: C, 62.12; H, 4.03; N, 9.88. Found: C, 62.15; H, 4.04; N, 9.85.

EXAMPLE 49

[5-(5,6-Difluoro-1H-indol-2-yl)-2-methoxy-phenyl] (4-hydroxy-3-nitro-benzyl)-amine 4-Hydroxy-3-nitrobenzaldehyde (0.334 g, 2.0 mmol) was added to a stirred mixture of 5-(5,6-difluoro-1H-indol-2-yl)-2-methoxy-phenylamine (0.548 g, 2.0 mmol) in methylene chloride (125 mL), followed by acetic acid (0.2 g). The resulting mixture was stirred at room temperature for 1 hour. Sodium triacetoxyborohydride (0.47 g, 2.2 mmol) was added in one portion, and the resulting homogeneous solution stirred at room temperature for 7 days. Saturated aqueous sodium bicarbonate solution (100 mL) was added and the mixture stirred for 2 hours. The mixture was shaken, the organic layer separated and dried over $Na_2SO_4$. The solvent was evaporated to give an orange solid. Recrystallization from methanol gave the product (300 mg), mp 195–196° C.

Calculated for $C_{22}H_{17}N_3O_4F_2$: C, 62.12; H, 4.03; N, 9.88. Found: C, 61.89; H, 4.30; N, 9.79.

EXAMPLE 50

[5-(5,6-Difluoro-1H-indol-2-yl)-2-methoxy-phenyl]- (4-cyano-benzyl)-amine

4-Cyanobenzaldehyde (0.262 g, 2.0 mmol) was added to a stirred mixture of 5-(5,6-difluoro-1H-indol-2-yl)-2-methoxy-phenylamine (0.548 g, 2.0 mmol) in methylene chloride (125 mL), followed by acetic acid (0.2 g). The resulting mixture was stirred at room temperature for 1 hour. Sodium triacetoxyborohydride (0.46 g, 2.2 mmol) was added in one portion, and the resulting homogeneous solution was stirred at room temperature for 4 days. Saturated aqueous sodium bicarbonate solution (100 mL) was added and the mixture stirred for 2 hours. The mixture was shaken, the organic layer separated and dried over $Na_2SO_4$. The solvent was evaporated to give a colorless gum. Recrystallization from methanol gave the product (300 mg), mp 158–159° C.

Calculated for $C_{23}H_{17}N_3OF_2$: C, 70.94; H, 4.40; N, 10.79. Found: C, 70.21; H, 4.64; N, 10.70.

EXAMPLE 51

[5-(5,6-Difluoro-1H-indol-2yl)-2-methoxy-phenyl]- (3-cyano-benzyl)-amine

3-Cyanobenzaldehyde (0.262 g, 2.0 mmol) was added to a stirred mixture of 5-(5,6-difluoro-1H-indol-2-yl)-2-methoxy-phenylamine (0.548 g, 2.0 mmol) in methylene chloride (125 mL), followed by acetic acid (0.2 g). The resulting mixture was stirred at room temperature for 1 hour. Sodium triacetoxyborohydride (0.46 g, 2.0 mmol) was added in one portion, and the resulting homogeneous solution stirred at room temperature for 3 days. Saturated aqueous sodium bicarbonate solution (100 mL) was added and the mixture stirred for 2 hours. The mixture was shaken, the organic layer separated and dried over $Na_2S_4$. The solvent was evaporated to give a white solid. Recrystallization from methanol gave the product (500 mg), mp 154–155° C.

Calculated for $C_{23}H_{17}N_3OF_2$: C, 70.94; H, 4.40; N, 10.79. Found: C, 70.42; H, 4.73; N, 10.59.

EXAMPLE 52

4-[5-(5,6-Difluoro-1H-indol-2-yl)-2-methoxy-phenylamino]-benzoic acid methyl ester Copper(II) acetate (0.8 g, 4.4 mmol) was added to a stirred mixture of 5-(5,6-difluoro-1H-indol-2-yl)-2-methoxy-phenylamine from Example 3 (1.2 g, 4.4 mmol), 4-carbomethoxybenzeneboronic acid prepared according to Smith et al., *J. Am. Chem. Soc.*, 1996;118:11099 (1.0 g, 5.6 mmol), triethylamine (0.45 g, 4.4 mmol), and finely ground 4-Angstrom molecular sieve (~2 g) in dichloromethane (100 mL) at room temperature and protected from moisture. After 24 hours, the mixture was diluted with dichloromethane (75 mL) and filtered through Celite. The filtrate was washed successively with 2N HCl (2×), water, 1 M aqueous $K_2CO_3$, water, and saturated brine, then dried over $MgSO_4$. The solvent was removed under reduced pressure to leave the crude product (0.6 g) as a semicrystalline residue, which was chromatographed on a column of silicagel in ethyl acetate/pet ether 35:65 to afford the pure product, mp 166–170° C.

Calculated for $C_{23}H_{18}F_2N_2O_3 \cdot 0.2$ EtOAc: C, 67.10; H, 4.64; N, 6.58. Found: C, 67.09; H, 4.59; N, 6:26.

EXAMPLE 53

[5-(5,6-Difluoro-1H-indol-2-yl)-2-methoxy-phenyl]- (3-benzyloxy-phenyl)-amine

Step A: Tris(3-benzyloxy-phenyl)bismuthane

A solution of 3-benzyloxybromobenzene (10.0 g, 38 mmol) in tetrahydrofuran (30 mL) was added dropwise to a stirred suspension of magnesium (0.92 g, 38 mmol) in tetrahydrofuran (25 mL) under an inert atmosphere at such a rate as to maintain gentle reflux, after initiation of the reaction with a few crystals of iodine. Following the addition the mixture was heated to reflux for 2 hours, then allowed to cool. Bismuth(III) chloride (3.1 g, 9.8 mmol) was added in one portion, followed by tetrahydrofuran (10 mL). After 16 hours the mixture was heated to reflux for 1 hour, then cooled to 0° C. to 5° C. while saturated aqueous $NH_4Cl$ (50 mL) was added dropwise. After 2 hours the mixture was filtered and the filtrate allowed to separate into layers. The organic layer was dried over $MgSO_4$, then stripped of solvent under reduced pressure. The residue was triturated in chloroform and filtered. The filtrate was stripped of solvent under reduced pressure to leave the product (6.6 g) as an oil sufficiently pure for the next step.

Step B. [5-(5,6-Difluoro-1H-indol-2-yl)-2-methoxy-phenyl]-(3-benzyloxy-phenyl)-amine Prepared according to the procedure described for Example 22 using 5-(5,6-difluoro-1H-indol-2-yl)-2-methoxy-phenylamine from Example 3 (1.1 g, 4.0 mmol), tris(3-benzyloxy-phenyl)bismuthane (2.9 g, 3.8 mmol), copper(II) acetate (0.76 g, 4.2 mmol), and triethylamine (0.42 g, 14.2 mmol) to afford the crude product as a brown oil (1.9 g). Chromatography on a column of silicagel in ether/pet ether 3:2 gave the product as a syrup, which was then treated with saturated hydrogen chloride ethanol (2–3 mL) to afford a crystalline product, mp 200–201° C. (dec).

Calculated for $C_{28}H_{22}F_2N_2O_2 \cdot 0.5$ HCl$\cdot$0.5 EtOH: C, 69.98; H, 5.16; N, 5.63. Found: C, 69.86; H, 5.21; N, 5.62.

EXAMPLE 54

[5-(5,6-Dichloro-1H-indol-2-yl)-2-methoxy-phenyl]-(3-trifluoro-methylphenyl)-amine Prepared according to the procedure described for Example 22 using 5-(5,6-dichloro-1H-indol-2-yl)-2-methoxy-phenylamine from Example 18 (1.0 g, 3.3 mmol), tris(3-tifluoromethyl-phenyl)bismuthane prepared according to Banfi et al., *Synthesis*, 1994:775–776 (2.1 g, 3.3 mmol), copper(II) acetate (0.7 g, 3.9 mmol), and triethylamine (0.34 g, 3.3 mmol) to afford the product (1.0 g). Recrystallization from acetonitrile afforded analytically pure material, mp 193–194° C.

Calculated for $C_{22}H_{15}Cl_2F_3N_2O$: C, 58.56; H, 3.35; N, 6.21. Found: C, 58.50; H, 3.17; N, 5.96.

D. Biological Assays

Inhibition of 15-LO

The 15-LO inhibitors of Formula I are effective for treating inflammation and atherosclerosis. A characteristic feature of atherosclerosis is the accumulation of cholesterol ester engorged from foam cells. Foam cells are derived from circulating monocytes which invade artery walls in response to hypercholesterolemia, and mature into tissue macrophages. The enzyme 15-LO has been implicated in inflammatory disorders and in the origin and recruitment of foam cells (see Harats et al., *Trends Cardiovasc. Med.*, 1995;5(1) :29–36). This enzyme is capable of oxidizing esterified polyenoic fatty acids, such as those found in phospholipids. Treatment of experimental animals with antioxidants which reduce hydroperoxides produced by 15-LO has been shown to retard the progression of atherosclerotic lesions. Accordingly, administering compounds which inhibit 15-LO is an effective way to treat and prevent atherosclerosis.

The compounds described above are effective inhibitors of 15-LO when evaluated in standard assays routinely utilized to measure 15-LO activity. Specifically, representative compounds were evaluated by the methods described by Auerbach et al., *Analytical Biochemistry*, 1992;201:375–380. Two in vitro assays were utilized, one utilizing rabbit reticulocyte 15-LO, the other using human 15-LO. Both used linoleic acid as substrate, to enzymatically produce a peroxide oxidation product known as 13(S)-HPODE. N-Benzoyl leucomethylene blue was utilized as a colorimetric reagent for detection and quantification of the peroxide formation. Also, HPLC was utilized to quantify the oxidation following incubation at 4° C. for 10 minutes.

The 15-LO inhibitory activity of representative compounds of Formula I is presented in Table 1. Data Column 1 gives the concentration of compound required to inhibit 50% of the activity of 15-LO ($IC_{50}$) when measured by the HPLC method of Auerbach et al. using rabbit enzymes, and data Column 2 gives data from human 15-LO enzyme.

TABLE 1

Pharmacological Data

| Example | Molstructure | Name | Data Column 1 $IC_{50}$ Rabbit Enzyme (nM) | Data Column 2 $IC_{50}$ Human Enzyme (nM) |
|---|---|---|---|---|
| 1 | | 5-(1H-Indol-2-yl)-2-methoxy-phenylamine | 113 | 23 |
| 2 | | 1-(3,5-Dichloro-phenyl)-3-[5-(1H-indol-2-yl)-2-methoxy-phenyl]-thiourea | 11 | 29 |

TABLE 1-continued
Pharmacological Data
| Example | Molstructure | Name | Data Column 1 IC$_{50}$ Rabbit Enzyme (nM) | Data Column 2 IC$_{50}$ Human Enzyme (nM) |
|---|---|---|---|---|
| 3 | 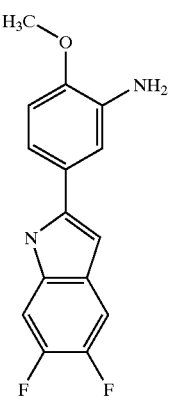 | 5-(5,6-Difluoro-1H-indol-2-yl)-2-methoxy-phenylamine | 27 | 53 |
| 4 | 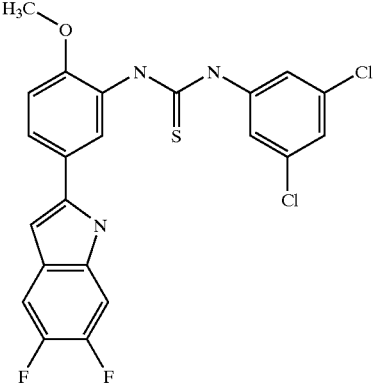 | 1-(3,5-Dichloro-phenyl)-3-[5-(5,6-difluoro-1H-indol-2-yl)-2-methoxy-phenyl]-thiourea | 30 | 60 |
| 5 | 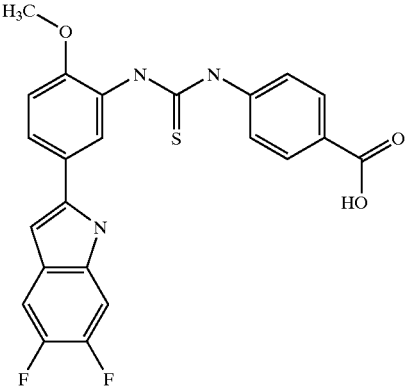 | 4-{3-[5-(5,6-Difluoro-1H-indol-2-yl)-2-methoxy-phenyl]-thioureido}-benzoic acid | 11 | 13 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 6 | | 3-{3-[5-(5,6-Difluoro-1H-indol-2-yl)-2-methoxy-phenyl]-thioureido}-benzoic acid | 2 | 25 |
| 7 | | N-[5-(5,6-Difluoro-1H-indol-2-yl)-2-methoxy-phenyl]-methanesulfonamide | 10 | 19 |
| 8 | | 3,5-Dichloro-N-[5-(5,6-difluoro-1H-indol-2-yl)-2-methoxy-phenyl]-benzenesulfonamide | 19 | 73 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 9 | 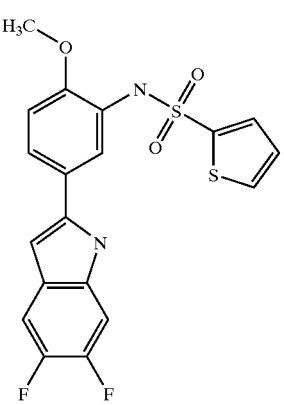 | Thiophene-2-sulfonic acid [5-(5,6-difluoro-1H-indol-2-yl)-2-methoxy-phenyl]-amide | 40 | 7 |
| 10 | 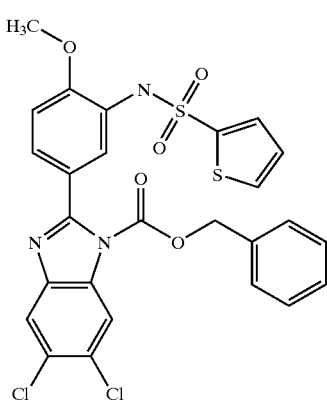 | 5,6-Dichloro-2-[4-methoxy-3-(thiophene-2-sulfonylamino)-phenyl]-benzoimidazole-1-carboxylic acid benzyl ester | 1390 | 81% inhibition at 10 micromolar |
| 11 | 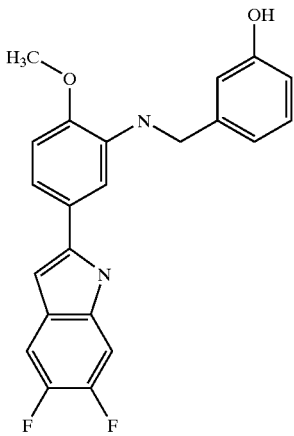 | 3-{[5-(5,6-Difluoro-1H-indol-2-yl)-2-methoxy-phenylamino]-methyl}-phenol | 24 | 106 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 12 | | [5-(56-Difluoro-1H-indol-2-yl)-2-methoxy-phenyl]-thiophen-2-ylmethyl-amine | 45 | 461 |
| 13 | | [5-(5,6-Difluoro-1H-indol-2-yl)-2-methoxy-phenyl]-(4-methoxy-benzyl)-amine | 40 | 414 |
| 14 | | 4-{[5-(5,6-Difluoro-1H-indol-2-yl)-2-methoxy-phenylamino]-methyl}-benzoic acid methyl ester | 113 | 1260 |

TABLE 1-continued
Pharmacological Data
| Example | Molstructure | Name | Data Column 1 IC$_{50}$ Rabbit Enzyme (nM) | Data Column 2 IC$_{50}$ Human Enzyme (nM) |
|---|---|---|---|---|
| 15 | 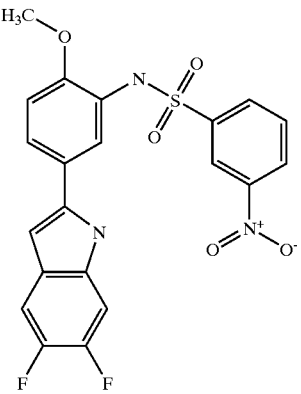 | N-[5-(5,6-Difluoro-1H-indol-2-yl)-2-methoxy-phenyl]-3-nitro-benzenesulfonamide | 124 | 49 |
| 16 | 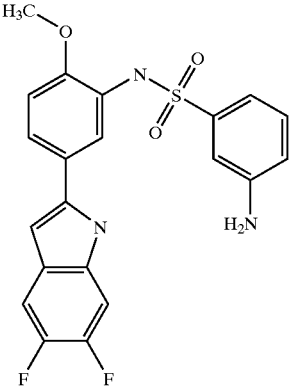 | 3-Amino-N-[5-(5,6-difluoro-1H-indol-2-yl)-2-methoxy-phenyl]-benzenesulfonamide | not tested | 20 |
| 17 | 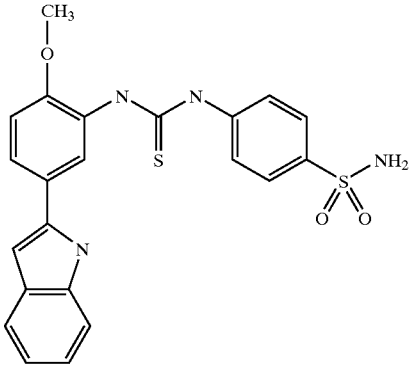 | 4-{3-[5-(1H-Indol-2-yl)-2-methoxy-phenyl]-thioureido}-benzenesulfonamide | no tested | 187 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 18 | | 5-(5,6-Dichloro-1H-indol-2-yl)-2-methoxy-phenylamine | 37 | 359 |
| 19 | | 3-{3-[5-(5,6-Dichloro-1H-indol-2-yl)-2-methoxy-phenyl]-thioureido}-benzoic acid | 13 | 254 |
| 20 | | Dodecane-1-sulfonic acid [5-(5,6-difluoro-1H-indol-2-yl)-2-methoxy-phenyl]-amide | not tested | 13 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 21 | | Dodecane-1-sulfonic acid [5-(5,6-dichloro-1H-benzoimidazol-2-yl)-2-methoxy-phenyl]-amide | not tested | 65% inhibition at 10 micromolar |
| 22 | | [5-(5,6-Difluoro-1H-indol-2-yl)-2-methoxy-phenyl]-(3-trifluoro-methylphenyl)-amine | not tested | 48 |
| 23 | | (4-{3-[5-(1H-Indol-2-yl)-2-methoxy-phenyl]-thioureido)-benzyl)-phosphonic acid diethyl ester | not tested | 331 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 24 | | (4-{3-[5-(5,6-Difluoro-1H-indol-2-yl)-2-methoxy-phenyl]-thioureido}-benzyl)-phosphonic acid diethyl ester | 18 | 91 |
| 25 | | 1-(3,5-Dichloro-phenyl)-3-[5-(5,6-difluoro-1H-indol-2-yl)-2-methoxy-phenyl]-urea | not tested | 2083 |
| 26 | | [5-(1H-Indol-2-yl)-2-methoxy-phenyl]-thiourea | not tested | 258 |

TABLE 1-continued
Pharmacological Data
| Example | Molstructure | Name | Data Column 1 IC$_{50}$ Rabbit Enzyme (nM) | Data Column 2 IC$_{50}$ Human Enzyme (nM) |
|---|---|---|---|---|
| 27 | 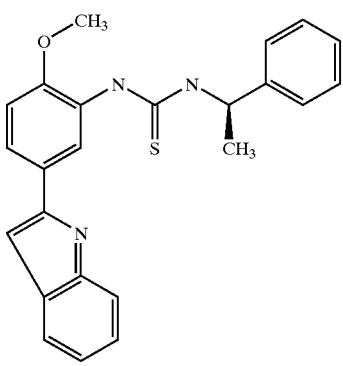 | 1-[5-(1H-Indol-2-yl)-2-methoxy-phenyl]-3-(1-phenyl-ethyl)-thiourea | not tested | 1770 |
| 28 | 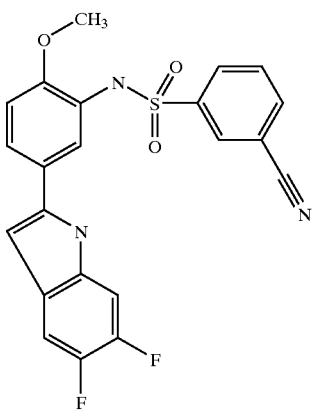 | 3-Cyano-N-[5-(5,6-difluoro-1H-indol-2-yl)-2-methoxy-phenyl]-benzenesulfonamide | not tested | 802 |
| 29 | 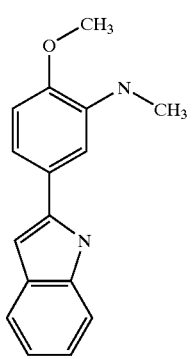 | [5-(1H-Indol-2-yl)-2-methoxy-phenyl]-methyl-amine | not tested | 470 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---------|--------------|------|-----|-----|
| 30 | | 5-{3-[5-(5,6-Difluoro-1H-indol-2-yl)-2-methoxy-phenyl]-thioureido}-isophthalic acid | not tested | 1817 |
| 31 | | (2-{3-[5-(1H-Indol-2-yl)-2-methoxy-phenyl]-thioureido}-ethyl)-carbamic acid tert-butyl ester | not tested | 141 |
| 32 | | 4-{3-[5-(1H-Indol-2-yl)-2-methoxy-phenyl]-thioureido}-benzoic acid | not tested | 304 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 33 | | (3-{3-[5-(1H-Indol-2-yl)-2-methoxy-phenyl]-thioureido}-phenyl)-acetic acid | not tested | 740 |
| 34 | | (4-{3-[5-(1H-Indol-2-yl)-2-methoxy-phenyl]-thioureido}-phenyl)-acetic acid | not tested | 1444 |
| 35 | | 1-[5-(5,6-Difluoro-1H-indol-2-yl)-2-methoxy-phenyl]-3-((S)-1-phenyl-ethyl)-thiourea | not tested | 538 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 36 | | (S)-3-tert-Butoxy-2-{3-[5-(5,6-Difluoro-1H-indol-2-yl)-2-methoxy-phenyl]-thioureido}-propionic acid tert-butyl ester | not tested | 51% inhibition at 10 micromolar |
| 37 | | 1-[5-(5,6-Difluoro-1H-indol-2-yl)-2-methoxy-phenyl]-3-(2-hydroxy-ethyl)-thiourea | 45 | 33 |
| 38 | | (2-{3-[5-(5,6-Difluoro-1H-indol-2-yl)-2-methoxy-phenyl]-thioureido)-ethyl)-carbamic acid tert-butyl ester | 19 | 25 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 39 | | 1-[5-(5,6-Difluoro-1H-indol-2-yl)-2-methoxy-phenyl]-3-(3,4-difluoro-phenyl)-thiourea | 17 | 36 |
| 40 | | 1-[5-(5,6-Difluoro-1H-indol-2-yl)-2-methoxy-phenyl]-3-((1S,2S)-2-hydroxy-1-hydroxymethyl-2-phenyl-ethyl)-thiourea | not tested | 620 |
| 41 | | 1-[5-(5,6-Difluoro-1H-indol-2-yl)-2-methoxy-phenyl]-3-pyridin-3-yl-thiourea | 5 | 10 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 42 | | [5-(1H-indol-2-yl)-2-methoxy-phenyl]-(3-nitro-benzyl)-amine | not tested | 870 |
| 43 | | [5-(1H-Indol-2-yl)-2-methoxy-phenyl]-(4-nitro-benzyl)-amine | not tested | 920 |
| 44 | | [5-(1H-indol-2-yl)-2-methoxy-phenyl]-(3-hydroxy-4-nitro-benzyl)-amine | not tested | 236 |
| 45 | | [5-(1H-indol-2-yl)-2-methoxy-phenyl]-4-hydroxy-3-nitro-benzyl)-amine | not tested | 420 |
| 46 | | [5-(5,6-Difluoro-1H-indol-2-yl)-2-methoxy-phenyl]-(3-nitro-benzyl)-amine | not tested | 3030 |

TABLE 1-continued

Pharmacological Data

| Example | Molstructure | Name | Data Column 1 IC$_{50}$ Rabbit Enzyme (nM) | Data Column 2 IC$_{50}$ Human Enzyme (nM) |
|---|---|---|---|---|
| 47 | 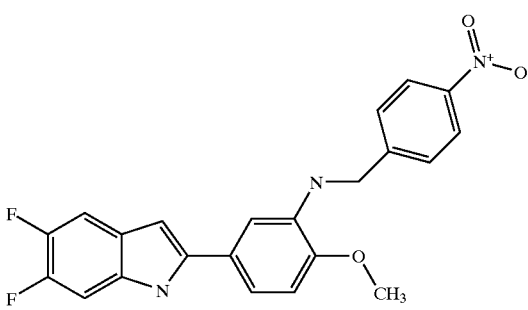 | [5-(5,6-Difluoro-1H-indol-2-yl)-2-methoxy-phenyl]-(4-nitro-benzyl)-amine | not tested | 534 |
| 48 | 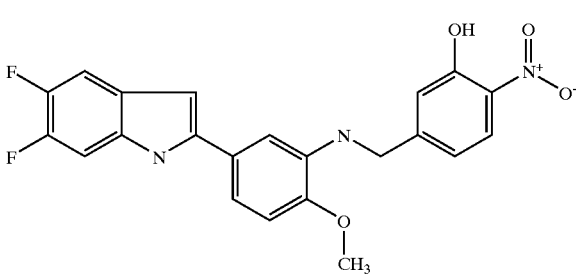 | [5-(5,6-Difluoro-1H-indol-2-yl)-2-methoxy-phenyl]-(3-hydroxy-4-nitro-benzyl)-amine | not tested | 98% inhibition at 10 micromolar |
| 49 | 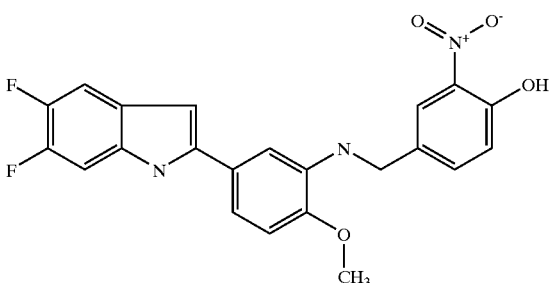 | 5-(5,6-Difluoro-1H-indol-2-yl)-2-methoxy-phenyl]-(4-hydroxy-3-nitro-benzyl)-amine | not tested | 99% inhibition at 10 micromolar |
| 50 | 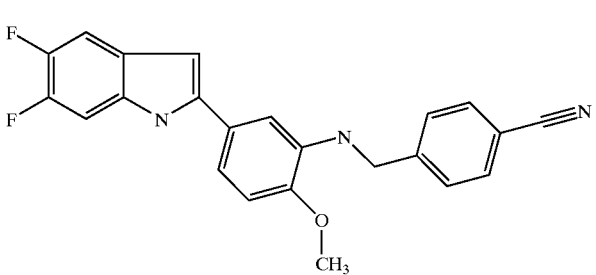 | [5-(5,6-Difluoro-1H-indol-2-yl)-2-methoxy-phenyl]-(4-cyano-benzyl)-amine | 74 | 116 |
| 51 | 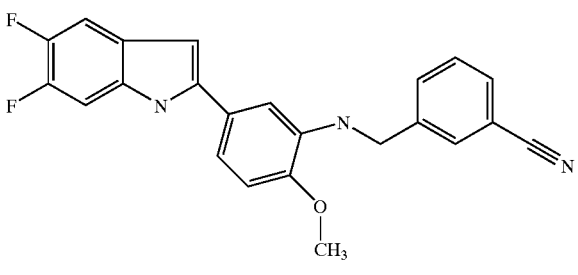 | [5-(5,6-Difluoro-1H-indol-2-yl)-2-methoxy-phenyl]-(3-cyano-benzyl)-amine | not tested | 432 |

TABLE 1-continued

Pharmacological Data

| Example | Molstructure | Name | Data Column 1 $IC_{50}$ Rabbit Enzyme (nM) | Data Column 2 $IC_{50}$ Human Enzyme (nM) |
|---|---|---|---|---|
| 52 | | 4-[5-(5,6-Difluoro-1H-indol-2-yl)-2-methoxy-phenylamino]-benzoic acid methyl ester | not tested | 31 |
| 53 | | [5-(5,6-Difluoro-1H-indol-2-yl)-2-methoxy-phenyl]-(3-benzyloxy-phenyl)-amine | 16 | 22 |
| 54 | | [5-(5,6-Dichloro-1H-indol-2-yl)-2-methoxy-phenyl]-(3-trifluoromethyl-phenyl)-amine | not tested | 127 |

Characterization of Atherosclerotic Lesions

Rabbits were euthanized by an overdose of sodium pentobarbital (150 mg/kg$^{-1}$) and exsanguinated via the abdominal aorta. Aortas were removed from the valve to the ileal bifurcation, opened to expose the intima, and photographed with a Polaroid camera. By use of these photographs, the areas of grossly discernible atherosclerosis were manually integrated on a digitizing pad and calculated with SigmaScan (Jandel Scientific). Aortas were visually subdivided into three areas: arch (aortic valve to first intercostal), thoracic aorta (first intercostal to diaphragm area), and abdominal aorta (diaphragm to ileal bifurcation). In addition to extracting aortas, body tissues were surveyed for indications of adverse reactions.

Determination of Cholesterol Esters and Unesterified Cholesterol Content

Weighed segments of each aortic region (arch, thoracic, and abdominal) were extracted. Esterified and unesterified cholesterol content of aortic tissue were determined by gas chromatography using 5-α-cholestane as an internal standard.

These data establish that administration of a 15-LO inhibitor effectively protects against the development of atherosclerosis in animals.

E. Uses

The disclosed compounds of Formula I will be formulated by standard methods into pharmaceutical compositions that are useful as prophylactic or therapeutic treatments for diseases modulated by the 15-LO cascade. The compositions will be administered to mammals for treating and preventing inflammation and atherosclerosis.

1. Dosages

Those skilled in the art will be able to determine, according to known methods, the appropriate dosage for a patient, talking into account factors such as age, weight, general health, the type of pain requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight 2. Formulations Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbents, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents. The following examples further illustrate typical pharmaceutical compositions provided by this invention.

EXAMPLE 55

| Tablet Formulation | |
|---|---|
| Ingredient | Amount (mg) |
| Indole of Example 1 | 25 |
| Lactose | 50 |
| Cornstarch (for mix) | 10 |
| Cornstarch (paste) | 10 |
| Magnesium stearate (1%) | 5 |
| Total | 100 |

The indole of Example 1, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administrated to a human from one to four times a day for treatment of atherosclerosis and inflammation.

EXAMPLE 56

| Preparation for Oral Solution | |
|---|---|
| Ingredient | Amount |
| Indole of Example 7 | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the indole of Example 7 is dissolved therein. The saccharin, sodium benzoate, flavor, and dye are added and dissolved. The volume is adjusted to 100 mL with distilled water. Each milliliter of syrup contains 4 mg of invention compound.

EXAMPLE 57

Parenteral Solution

In a solution of 700 mL of propylene glycol and 200 mL of water for injection is suspended 20 g of the benzimidazol of Example 21. After suspension is complete, the pH is adjusted to 6.5 with 1N sodium hydroxide, and the volume is made up to 100 mL with water for injection. The formulation is sterilized, filled into 5.0-mL ampoules each containing 2.0 mL, and sealed under nitrogen.

F. Other Embodiments

From the above disclosure and examples, and from the claims below, the essential features of the invention are readily apparent. The scope of the invention also encompasses various modifications and adaptations within the knowledge of a person of ordinary skill. Examples include a disclosed compound modified by addition or removal of a protecting group, or the formation of an ester, pharmaceutical salt, hydrate, acid, or amide of a disclosed compound. Publications cited herein are hereby incorporated by reference in their entirety.

What is claimed is:

1. A compound of Formula II

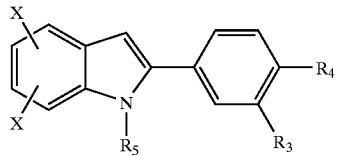

wherein:
- $R_3$ is $NHR_a$, where $R_a$ is H, $C_1$–$C_4$ alkyl, $C_3$–$C_8$ cycloalkyl, phenyl, $C_2$–$C_6$ heteroaryl, benzyl, $CH_2$—($C_2$–$C_6$ heterocyclic radical), $CONR_b$, $CSNR_b$, $SO_2R_b$, $SO_2T$, $CONR_bT$, $CSNR_bT$, T is $C_1$–$C_{18}$ alkyl, phenyl, or $C_3$–$C_6$ heterocyclic radical; and $R_b$ is H, $C_1$–$C_4$ alkyl, phenyl, benzyl, $C_1$–$C_6$ alkoxy, $C_1$–$C_6$ alkanoic acid alkyl ester; $C_1$–$C_6$-alkylamino carbarnate, 1-phenethyl, 2-phenethyl, aminosulfonylphenyl, an amino acid radical selected from serine, phenylalanine, histidine, tryptophan, or tyrosine wherein hydroxy or carboxy groups may be protected or unprotected linked by the amino nitrogen or $C_2$–$C_6$ heterocyclic radical;
- $R_4$ is selected from methoxy, ethoxy, thiomethoxy, fluoro, chloro, methyl, and ethyl; ($C_1$–$C_4$ alkyl)oxycarbonyl, ($C_3$–$C_8$ cycloalkyl)-oxycarbonyl, ($C_3$–$C_8$ cycloalkyl)-($C_1$–$C_4$ alkyl)oxycarbonyl, or ($C_6$–$C_{10}$ aryl) oxycarbonyl;
- $R_5$ is H, [phenyl($C_1$–$C_4$ alkyl)]oxycarbonyl, ($C_1$–$C_4$ alkyl)oxycarbonyl, ($C_3$–$C_8$ cycloalkyl)oxycarbonyl, ($C_3$–$C_8$ cycloalkyl)-($C_1$–$C_4$ alkyl)oxycarbonyl, or ($C_6$–$C_{10}$ aryl)oxycarbonyl;
- $R_6$ is H or $C_1$–$C_6$ alkyl;
- each X is independently H, halo, $C_1$–$C_4$ alkyl, $C_1$–$C_4$ alkenyl, $C_1$–$C_4$ alkynyl, hydroxyl, $C_1$–$C_4$ hydroxyalkyl, amino, (amino)sulfonyl, N-acetyl, O-acetyl, $C_1$–$C_4$ thioalkyl, $C_1$–$C_4$ alkoxy, $COOR_6$, $SO_3Na$, $SO_3H$, $SO_2NH_2$, cyano, phosphonic acid, phosphonic acid esters, $C_1$–$C_6$ alkanoic acid, $C_1$–$C_6$ alkanoic acid caters, carbamic acid, carbamic acid esters, $CH_2NH_2$, acetyl, di($C_1$–$C_4$ alkyl)amino, or nitro;

or a pharmaceutically acceptable salt thereof.

2. A compound selected from:
5-(1H-indol-2-yl)-2-methoxy-phenylamine;
5-(5,6-Difluoro-1H-indol-2-yl)-2-methoxy-phenylamine;
4-{3-[5-(5,6-Difluoro-1H-indol-2-yl)-2-methoxy-phenyl]-thioureido}-benzoic acid;
3-{3-[5-(5,6-Difluoro-1H-indol-2-yl)-2-methoxy-phenyl]-thioureido}-benzoic acid;
N-[5-(5,6-Difluoro-1H-indol-2-yl)-2-methoxy-phenyl]-methanesulfonamide;
Thiophene-2-sulfonic acid [5-(5,6-difluoro-1H-indol-2-yl)-2-methoxy-phenyl]-amide;
3-Amino-N-[5-(5,6-difluoro-1H-indol-2-yl)-2-methoxy-phenyl]-benzenesulfonamide;
[5-(5,6-Difluoro-1H-indol-2-yl)-2-methoxy-phenyl]-(3-trifluoro-methylphenyl)-amine;
1-[5-(5,6-Difluoro-1H-indol-2-yl)-2-methoxy-phenyl]-3-(2-hydroxy-ethyl)-thiourea;
(2-{3-[5-(5,6-Difluoro-1H-indol-2-yl)-2-methoxy-phenyl]-thioureido}-ethyl)-carbamic acid tert-butyl ester;
1-[5-(5,6-Difluoro-1H-indol-2-yl)-2-methoxy-phenyl]-3-pyridin-3-yl-thiourea;
[5-(5,6-Difluoro-1H-indol-2-yl)-2-methoxy-phenyl]-(3-hydroxy-4-nitro-benzyl)-amine;
5-(5,6-Difluoro-1H-indol-2yl)-2-methoxy-phenyl]-(4-hydroxy-3-nitro-benzyl)-amine;
4-[5-(5,6-Difluoro-1H-indol-2-yl)-2-methoxy-phenylamino]-benzoic acid methyl ester; and
[5-(5,6-Difluoro-1H-indol-2-yl)-2-methoxy-phenyl]-(3-benzyloxy-phenyl)-amine.

3. A compound selected from:
5-(1H-Indol-2-yl)-2-methoxy-phenylamine hydrochloride;
1-(3,5-Dichloro-phenyl)-3-[5-(1H-indol-2-yl)-2-methoxy-phenyl]-thiourea;
5-(5,6-Difluoro-1H-indol-2-yl)-2-methoxy-phenylamine hydrochloride;
1-(3,5-Dichloro-phenyl)-3-[5-(5,6-difluoro-1H-indol-2-yl)-2-methoxy-phenyl]-thiourea;
4-{3-[5-(5,6-Difluoro-1H-indol-2-yl)-2-methoxy-phenyl]-thioureido}-benzoic acid sodium salt;
3-{3-[5-(5,6-Difluoro-1H-indol-2-yl)-2-methoxy-phenyl]-thioureido}-benzoic acid;
3,5-Dichloro-N-[5-(5,6-difluoro-1H-indol-2-yl)-2-methoxy-phenyl]-benzenesulfonamide;
3-{[5-(5,6-Difluoro-1H-indol-2-yl)-2-methoxy-phenylamino]-methyl}-phenol;
[5-(5,6-Difluoro-1H-indol-2-yl)-2-methoxy-phenyl]-thiophen-2-ylmethyl]-amine;
[5-(5,6-Difluoro-1H-indol-2-yl)-2-methoxy-phenyl]-(4-methoxy-benzyl)-amine;
4-{[5-(5,6-Difluoro-1H-indol-2-yl)-2-methoxy-phenylamino]-methyl}-benzoic acid methyl ester;
N-[5-(5,6-Difluoro-1H-indol-2-yl)-2-methoxy-phenyl]-3-nitro-benzenesulfonamide;
3-Amino-N-[5-(5,6-difluoro-1H-indol-2-yl)-2-methoxy-phenyl]-benzenesulfonamide hydrochloride;
4-{3-[5-(1H-Indol-2-yl)-2-methoxy-phenyl]-thioureido}-benzenesulfonamide;
5-(5,6-Dichloro-1H-indol-2-yl)-2-methoxy-phenylamine;
3-{3-[5-(5,6-Dichloro-1H-indol-2-yl)-2-methoxy-phenyl]-thioureido}-benzoic acid;
Dodecane-1-sulfonic acid [5-(5,6-diflouro-1H-indol-2-yl)-2-methoxy-phenyl]-amide;
[5-(5,6-Difluoro-1H-indol-2-yl)-2-methoxy-phenyl]-(3-trifluoro-methylphenyl)-amine hydrochloride;
(4-{3-[5-(1H-Indol-2-yl)-2-methoxy-phenyl]-thioureido}-benzyl)-phosphonic acid diethyl ester;
(4-{3-[5-(5,6-Difluoro-1H-indol-2-yl)-2-methoxy-phenyl]-thioureido}-benzyl)-phosphonic acid diethyl ester;
1-(3,5-Dichloro-phenyl)-3-[5-(5,6-difluoro-1H-indol-2-yl)-2-methoxy-phenyl]-urea;
[5-(1H-Indol-2-yl)-2-methoxy-phenyl]-thiourea;
1-[5-(1H-Indol-2-yl)-2-methoxy-phenyl]-3-(1-phenyl-ethyl)-thiourea;
3-Cyano-N-[5-(5,6-difluoro-1H-indol-2-yl)-2-methoxy-phenyl]-benzenesulfonamide;
[5-(1H-Indol-2-yl)-2-methoxy-phenyl]-methyl-amine;
5-{3-[5-(5,6-Difluoro-1H-indol-2-yl)-2-methoxy-phenyl]-thioureido}-isophthalic acid;
(2-{3-[5-(1H-Indol-2-yl)-2-methoxy-phenyl]-thioureido}-ethyl)-carbamic acid tert-butyl ester;
4-{3-[5-(1H-Indol-2-yl)-2-methoxy-phenyl]-thioureido}-benzoic acid;
(3-{3-[5-(1H-Indol-2-yl)-2-methoxy-phenyl]-thioureido}-phenyl}-acetic acid;
(4-{3-[5-(1H-Indol-2-yl)-2-methoxy-phenyl]-thioureido}-phenyl)-acetic acid;
1-[5-(5,6-Difluoro-1H-indol-2-yl)-2-methoxy-phenyl]-3-((S)-1-phenyl-ethyl)-thiourea;
(S)-3-tert-Butoxy-2-{3-[5-(5,6-Difluoro-1H-indol-2-yl)-2-methoxy-phenyl]-thioureido}-propionic acid tert-butyl ester;

1-[5-(5,6-Difluoro-1H-indol-2-yl)-2-methoxy-phenyl]-3-(3,4-difluoro-phenyl)-thiourea;

1-[5-(5,6-Difluoro-1H-indol-2-yl)-2-methoxy-phenyl]-3-((1S,2S)-2-hydroxy-1-hydroxymethyl-2-phenyl-ethyl)-thiourea;

1-[5-(5,6-Difluoro-1H-indol-2-yl)-2-methoxy-phenyl]-3-pyridin-3-yl-thiourea hydrochloride;

[5-(1H-indol-2-yl)-2-methoxy-phenyl]-(3-nitro-benzyl)-amine;

[5-(1H-Indol-2-yl)-2-methoxy-phenyl]-(4-nitro-benzyl)-amine;

[5-(1H-indol-2-yl)-2-methoxy-phenyl]-(3-hydroxy-4-nitro-benzyl)-amine;

[5-(1H-indol-2-yl)-2-methoxy-phenyl]-(4-hydroxy-3-nitro-benzyl)-amine;

[5-(5,6-Difluoro-1H-indol-2-yl)-2-methoxy-phenyl]-(3-nitro-benzyl)-amine;

[5-(5,6-Difluoro-1H-indol-2-yl)-2-methoxy-phenyl]-(4-(nitro-benzyl)-amine;

[5-(5,6-Difluoro-1H-indol-2-yl)-2-methoxy-phenyl]-(3-hydroxy-4-nitro-benzyl)-amine hydrochloride;

5-(5,6-Difluoro-1H-indol-2-yl)-2-methoxy-phenyl]-(4hydroxy-3-nitro-benzyl)-amine hydrochloride;

[5-(5,6-Difluoro-1H-indol-2-yl)-2-methoxy-phenyl]-(4-cyano-benzyl)-amine;

[5-(5,6-Difluoro-1H-indol-2-yl)-2-methoxy-phenyl]-(3-cyano-benzyl)-amine;

4-[5-(5,6-Difluoro-1H-indol-2-yl)-2-methoxy-phenylamino]-benzoic acid methyl ester hydrochloride;

[5-(5,6-Difluoro-1H-indol-2-yl)-2-methoxy-phenyl]-(3-benzyloxy-phenyl)-amine hydrochloride; and

[5-(5,6-Dichloro-1H-indol-2-yl)-2-methoxy-phenyl]-(3-trifluoromethyl-phenyl)-amine.

4. A compound of claim 1, wherein X is independently Cl, F, or H.

5. A compound of claim 4, wherein X are each F.

6. A compound of claim 4, wherein X are each Cl.

7. A compound of claim 4, wherein X are each H.

8. A compound of claim 4, wherein $R_a$ is H, methyl, ethyl, hydroxy ethyl, furanyl, phenyl, substituted phenyl, benzyl, or substituted benzyl.

9. A compound of claim 4, wherein $R_a$ is $CONR_b$, $CSNR_b$; $SO_2R_b$, $SO_2T$, $SO_2NR_bT$, $CONR_bT$, $CSNR_bT$;

T is $C_1$–$C_{18}$ alkyl, phenyl, or $C_3$–$C_6$ heterocyclic radical; and $R_b$ is H, $C_1$–$C_4$ alkyl, phenyl, benzyl, $C_1$–$C_6$ alkoxy, $C_1$–$C_6$ alkanoic acid alkyl ester, $C_1$–$C_6$-alkylamino carbamate, 1-phenethyl, 2-phenethyl, or aminosulfonylphenyl.

10. A compound of claim 9, wherein $R_4$ is methoxy.

11. A compound of claim 10, wherein $R_5$ is H.

12. A compound of claim 4, wherein $R_a$ is dichlorophenyl, carboxylic acid phenyl, aminosulfonylphenyl, dicarboxylic acid phenyl, or carboxylic acid benzyl.

\* \* \* \* \*